(12) United States Patent
Sanz Yague et al.

(10) Patent No.: US 10,301,241 B2
(45) Date of Patent: May 28, 2019

(54) PROCESS FOR THE PREPARATION OF HIGHER ALCOHOLS FROM LOWER ALCOHOLS BY GUERBET CONDENSATION

(71) Applicant: Abengoa Bioenergia Nuevas Tecnologies, S.A., Seville (ES)

(72) Inventors: Juan Luis Sanz Yague, Seville (ES); Jose David Martinez Perez, Seville (ES); Yolanda Pena Gomez, Seville (ES); Carmen Maria Reyes Valle, Seville (ES); Mario Ramos Sanchez, Seville (ES)

(73) Assignee: Abengoa Bioenergia Nuevas Tecnologias, S.A., Seville (ES)

( * ) Notice: Subject to any disclaimer, the term of this patent is extended or adjusted under 35 U.S.C. 154(b) by 225 days.

(21) Appl. No.: 15/108,444

(22) PCT Filed: Dec. 24, 2014

(86) PCT No.: PCT/EP2014/079306
§ 371 (c)(1),
(2) Date: Jun. 27, 2016

(87) PCT Pub. No.: WO2015/097285
PCT Pub. Date: Jul. 2, 2015

(65) Prior Publication Data
US 2016/0326075 A1 Nov. 10, 2016

(30) Foreign Application Priority Data

Dec. 27, 2013 (EP) ..................................... 13382570
Dec. 27, 2013 (EP) ..................................... 13382572

(Continued)

(51) Int. Cl.
*C07C 29/34* (2006.01)

(52) U.S. Cl.
CPC ............. *C07C 29/34* (2013.01); *Y02P 20/132* (2015.11)

(58) Field of Classification Search
CPC .................................................... C07C 29/34
See application file for complete search history.

(56) References Cited

U.S. PATENT DOCUMENTS 1,992,480 A 2/1935 Fuchs et al.
2,004,350 A 6/1935 Scott (Continued)

FOREIGN PATENT DOCUMENTS

WO 9104242 A1 4/1991
WO WO 91/04242 * 4/1991 ............. C07C 29/34

OTHER PUBLICATIONS

European Search Report for EP 13 38 2570, dated Jun. 4, 2014, 5 pgs.

(Continued)

*Primary Examiner* — Yate' K Cutliff
(74) *Attorney, Agent, or Firm* — Armstrong Teasdale LLP

(57) ABSTRACT

The present invention generally relates to processes for preparation of higher alcohols such as n-butanol from lower alcohols such as ethanol by Guerbet condensation. In some aspects, the present invention relates to improvements in n-butanol yield and selectivity by the selection of process reaction conditions such as, but not limited to, mole ratio of hydrogen to ethanol, mole ratio of acetaldehyde to ethanol, mole ratio of ethyl acetate to ethanol and/or mole ratio of carbon monoxide to ethanol.

7 Claims, 8 Drawing Sheets

(30) Foreign Application Priority Data

Dec. 27, 2013 (EP) .................................... 13382573
Dec. 27, 2013 (EP) .................................... 13382574

(56) References Cited

U.S. PATENT DOCUMENTS

| | | | |
|---|---|---|---|
| 2,762,847 A * | 9/1956 | Miller | C07C 29/34 568/905 |
| 2,836,628 A * | 5/1958 | Miller | A61K 8/342 523/122 |
| 2,862,013 A * | 11/1958 | Miller | C07C 29/34 508/463 |
| 3,479,412 A * | 11/1969 | Conti | C07C 29/34 568/700 |
| 5,300,695 A | 4/1994 | Radlowski | |
| 7,700,812 B2 | 4/2010 | Kourtakis et al. | |
| 8,071,823 B2 | 12/2011 | Ozer et al. | |
| 8,318,990 B2 | 11/2012 | Tanaka et al. | |
| 9,266,096 B2 | 2/2016 | Arjona Antolin et al. | |
| 9,475,741 B2 | 10/2016 | Arjona Antolin et al. | |
| 2010/0174121 A1 | 7/2010 | Manzer et al. | |
| 2010/0298613 A1 * | 11/2010 | Tanaka | C07C 29/34 568/905 |
| 2012/0271085 A1 | 10/2012 | Nesterenko et al. | |
| 2012/0323050 A1 | 12/2012 | Lee et al. | |
| 2013/0116481 A1 | 5/2013 | Wass et al. | |
| 2016/0326075 A1 | 11/2016 | Sanz Yague et al. | |

OTHER PUBLICATIONS

European Search Report for EP 13 38 2572, dated Jun. 4, 2014, 6 pgs.
European Search Report for EP 13 38 2573, dated Jun. 4, 2014, 6 pgs.
European Search Report for EP 13 38 2574, dated Jun. 4, 2014, 6 pgs.
International Search Report and Written Opinion for Application No. PCT/EP2014/0796306, dated Apr. 21, 2015, 11 pgs.
International Preliminary Report on Patentability for Application No. PCT/EP2014/0796306, dated Jun. 28, 2016, 7 pgs.

* cited by examiner

PROCESS FOR THE PREPARATION OF HIGHER ALCOHOLS FROM LOWER ALCOHOLS BY GUERBET CONDENSATION

CROSS-REFERENCE TO RELATED APPLICATIONS

This application claims the priority of International Application No. PCT/EP2014/079306 filed on Dec. 24, 2014, European Application No. EP 13382570.3 filed on Dec. 27, 2013, European Application No. EP 13382572.9 filed on Dec. 27, 2013, European Application No. EP 13382573.7 filed on Dec. 27, 2013 and European Application No. EP 13382574.5 filed on Dec. 27, 2013, each of which is incorporated by reference in its entirety.

BACKGROUND OF THE INVENTION

The field of the invention relates generally to processes for the preparation of higher alcohols from lower alcohols by Guerbet condensation.

Ethanol is the major liquid biofuel manufactured worldwide. However, there are still many problems associated with the use of ethanol fuel in internal combustion engines, including its water solubility, corrosivity and the differences in its fuel properties compared to gasoline. In order to overcome the disadvantages of ethanol as a fuel, catalytic condensation of lower alcohols (e.g., ethanol) to higher alcohols (e.g., n-butanol) can be carried out. Compared to ethanol, n-butanol has several advantages. For instance, n-butanol can be burned in the existing gasoline engines without practically any engine or car modifications and it has higher energy content and air-to-fuel ratio. Thus n-butanol an excellent green replacement for gasoline.

n-butanol can be obtained by means of the well-known Guerbet reaction, which makes it possible to catalytically convert a low-molecular-weight alcohol (e.g. ethanol) into a linear or branched alcohol with a higher molecular weight. The main disadvantages associated with the Guerbet reaction are the production of water, which must be eliminated from the reaction medium in order to favor the formation of the desired compounds; the production of side products including aldehydes, non-target alcohols, and carboxylic acids; and limited selectivity to n-butanol, limited ethanol conversion, and concomitant low butanol yield.

A need therefore exists for improved processes for the generation of higher alcohols by Guerbet condensation of lower alcohols.

BRIEF DESCRIPTION OF THE INVENTION

In one aspect of the present invention, a continuous process for preparing n-butanol is provided. The process comprises forming a reaction mixture comprising ethanol, hydrogen, water and acetaldehyde, the reaction mixture comprising a mole ratio of hydrogen to ethanol of from 0.1:1 to about 5:1, a mole ratio of acetaldehyde to ethanol of from about 0.001:1 to about 0.1:1, and a mole ratio of water to ethanol of less than about 0.05:1. The reaction mixture is contacted with a Guerbet catalyst in a gas phase reactor having a fixed catalyst bed at a reaction temperature of from about 50° C. to about 450° C. and a reaction pressure of from about 1 MPa absolute (10 bara) to about 20 MPa absolute (200 bara) to form a reactor product stream comprising n-butanol. The n-butanol yield based on ethanol is from about 10% to about 35% and the selectivity to n-butanol is from about 65% to about 95%.

In another aspect of the present disclosure, a continuous process for preparing n-butanol is provided. The process comprises forming a reaction mixture comprising (i) a source of ethanol comprising recovered ethanol and fresh ethanol, (ii) a source of hydrogen comprising recovered hydrogen and (iii) recovered acetaldehyde. The reaction mixture is contacted with a Guerbet catalyst in a gas phase reactor having a fixed catalyst bed to form a reactor product stream comprising n-butanol, hydrogen, ethanol, water, acetaldehyde, and ethyl acetate. The reactor product stream is fractionated to form (i) a first overhead gas stream comprising the recovered hydrogen and the recovered acetaldehyde, (ii) a first overhead condensate stream comprising ethanol, water, acetaldehyde and ethyl acetate, and (iii) a first bottoms stream comprising n-butanol. The first overhead stream is fractionated to form a second overhead stream enriched in acetaldehyde and ethyl acetate and a second bottoms stream comprising ethanol, water and no more than trace amounts of acetaldehyde and ethyl acetate. The second bottoms stream is fractionated to form the recovered ethanol, the recovered ethanol having reduced water content as compared to the second bottoms stream, and the first bottoms stream is fractionated to isolate n-butanol.

In another aspect of the present disclosure, a continuous process for preparing n-butanol is provided. The process comprises adding a reaction mixture comprising ethanol and acetaldehyde to a gas phase reactor having a fixed catalyst bed. The reaction mixture is added in a reactor feed section, the reactor feed section defined by a first reaction mixture addition site and a last reaction mixture addition site located along a length of the reactor, the reactor section from the first reaction mixture addition site to the last reaction mixture addition site being the reactor feed section. The reaction mixture is contacted with a Guerbet catalyst in the reactor at a temperature of from about 50° C. to about 450° C. and a pressure of from about 1 MPa absolute (10 bara) to about 20 MPa absolute (200) bara to form a reactor product stream comprising n-butanol. The average mole ratio of acetaldehyde to ethanol in the reaction mixture in the reactor feed section is from about 0.001:1 to about 0.05:1 and the acetaldehyde concentration profile in the reactor feed section is such that the mole ratio of acetaldehyde to ethanol in any region of the reactor feed section does not differ by more than 50% from the average mole ratio of acetaldehyde to ethanol in the reactor feed section. The n-butanol yield based on ethanol in the reactor product stream is from about 10% to about 35%, and the selectivity to n-butanol in the reactor product stream is from about 65% to about 95%.

In another aspect of the present invention, a continuous process for preparing n-butanol is provided. The process comprises forming a reaction mixture comprising (i) a source of ethanol comprising recovered ethanol and fresh ethanol, (ii) a source of hydrogen comprising recovered hydrogen and (iii) recovered acetaldehyde. The reaction mixture is contacted with a Guerbet catalyst in a gas phase reactor having a fixed catalyst bed to form a reactor product stream comprising n-butanol, hydrogen, ethanol, water, acetaldehyde, and ethyl acetate. The reactor product stream is fractionated to form (i) a reactor product gas stream comprising the recovered hydrogen and the recovered acetaldehyde and (ii) a reactor product condensate stream comprising n-butanol, the recovered ethanol, water, acetaldehyde and ethyl acetate. The reactor product condensate stream is fractionated in an extractive distillation apparatus with an extractive agent comprising regenerated extractive agent to form (i) an extractive distillation overhead stream comprising the recovered ethanol and (ii) an extractive distillation bottoms stream comprising n-butanol, water and the extractive agent. The extractive distillation bottoms stream is fractionated in a regeneration column to form (i) an overhead stream comprising n-butanol and (ii) a bottoms stream comprising regenerated extractive agent. The regeneration column overhead stream is fractionated to isolate n-butanol.

DETAILED DESCRIPTION OF THE INVENTION

Figure 1:
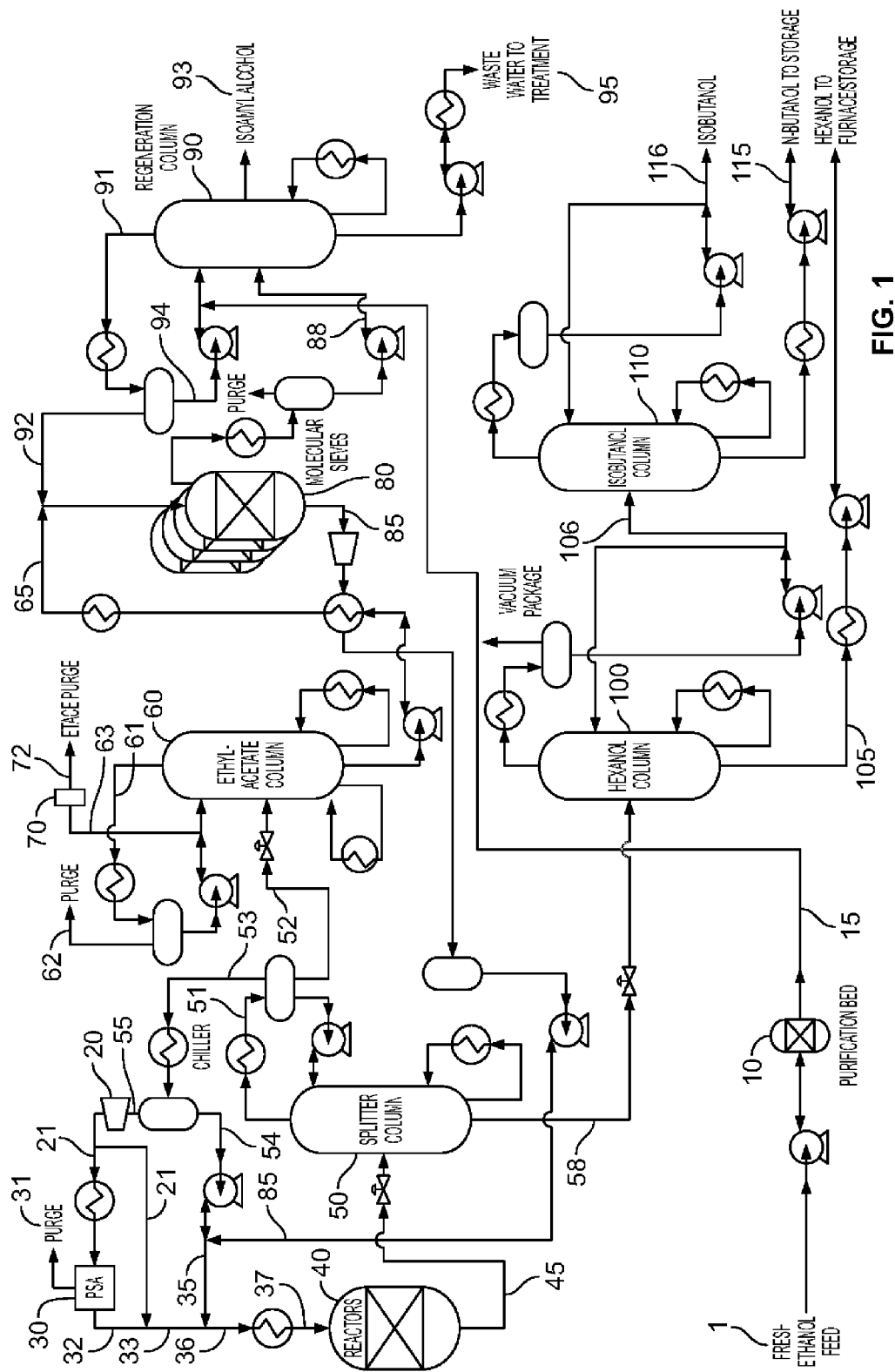
FIG. 1 is a process flow diagram of a first aspect of the present invention.

The present invention generally relates to a catalytic process for producing $C_3$ to $C_{15}$ higher alcohols, preferably $C_3$ to $C_8$ alcohols, from lower alcohols by Guerbet condensation. Guerbet condensation involves the catalytic condensation of alcohols under conditions of elevated temperature and pressure by a dehydrogenation, aldol condensation and hydrogenation sequence as follows:

(1)

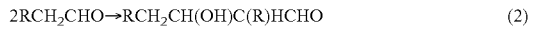(2)

(3)

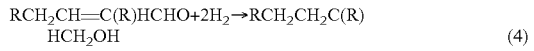(4)

Other linear and branched alcohols of higher molecular weight (e.g., $C_6$ to $C_8$ alcohols) can be obtained by successive condensation reactions between the starting alcohol and the alcohol produced.

For the preparation of butanol from ethanol, the reaction sequence may be described as follows:

(5)

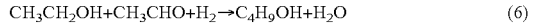(6)

And the overall reaction is as follows:

(7)

In accordance with the present invention, it has been discovered that starting alcohol (e.g., ethanol) conversion rate, selectivity to Guerbet alcohol (e.g., n-butanol) and Guerbet alcohol yield are generally affected by a number of factors. It has been further discovered that optimization of those factors, and combinations thereof, enable the preparation of Guerbet alcohols in high selectivity and yield. For instance, the following non-limiting list of factors has been discovered to affect the efficiency of the Guerbet reaction of the present invention: (i) the catalyst, catalyst loading and catalyst life, (ii) the concentration of various impurities and co-reactants in the reactor feed stream and various recycle streams, for instance and without restriction, water, hydrogen, carbon monoxide, acetaldehyde, and ethyl acetate, (iii) the ratios of said impurities and co-reactants to starting alcohol, (iv) reaction temperature, (v) reaction pressure, (vi) reactor liquid hourly space velocity ("LHSV"), wherein LHSV refers to the quotient of the entering volumetric flow rate of the reactants divided by the reactor volume and is an indication of the number of reactor volumes of reactant feed that can be treated in a unit time; and (vii) selected combinations of one or more of (i) to (vi).

As used herein, the terms "$C_3$ to $C_{15}$ higher alcohols" is understood to mean any linear or branched alkyl chain with at least one hydroxyl functional group which has between 3 and 15 carbon atoms. Non-limiting examples are propanol, isopropanol, n-butanol, 2-butanol, 2-methyl-2-butanol, 3-methyl-1-butanol-1-pentanol, 2-pentanol, 3-pentanol, 2,2-dimethyl-1-propanol, 3-methyl-2-butanol, 1,5-pentanediol, 2,4-pentanediol, 2,2-dimethyl-1,3-propanediol, 1,2-butanediol, 1,3-butanediol, 1,4-butanediol, 2,3-butanediol, 1-heptanol, 2-heptanol, 3-heptanol, 4-heptanol, 2-methyl-2-hexanol, 2,2-dimethyl-3-pentanol-1-octanol, 2-octanol, 3-octanol, 4-octanol, 2-ethyl-1-hexanol, 3-ethyl-1-hexanol and 2,2-dimethyl-3-hexanol. When the reagent is a $C_3$, the higher alcohol obtained will be at least a $C_4$, preferably a $C_4$, $C_5$, $C_6$, $C_7$ or $C_8$ alcohol. As used herein, "condensate" refers to a process stream predominantly comprising condensed liquids at the temperature and pressure thereof, but not excluding the present of some amount of gas or vapor. As used herein, "gas" and "vapor" are used interchangeably and may comprise condensable compounds (e.g., ethanol) and essentially non-condensable compounds (e.g., hydrogen), and does not exclude the possibility of some liquid entrainment. As used herein, "predominantly" means greater than 50%, at least 75%, at least 90% or at least 95% on a population %, w/w %, w/v % or v/v % basis. As used herein, "trace amount" and "essential absence" refer to a detectable, but minor amount, such as less than about 0.05 mole % or less than about 0.01 mole %.

Although specific reference to n-butanol is made herein, the present invention is useful for improved processes for the preparation of $C_3$ to $C_{15}$ higher alcohols, such as $C_3$ to $C_{15}$ alcohols, by Guerbet condensation.

Various non-limiting aspects of the present invention are depicted in FIGS. 1 to 8.

FIG. 1 depicts a first aspect of the process of the present invention wherein fresh ethanol feed 1 is optionally passed through purification bed 10 for removal of impurities (e.g., salts and ions) to form a fresh ethanol feed stream 15 comprising ethanol and water. In some aspects of the present invention, fresh ethanol may comprise isoamyl alcohol. Feed stream 15 is then processed in regeneration column 90. A molecular sieve 80 water rich feed stream 88 comprising ethanol is also processed in regeneration column 90. Regeneration column 90 separates water and isoamyl alcohol from ethanol to form regeneration column bottoms stream 95 comprising water that is sent to waste water treatment, isoamyl alcohol stream 93 and regeneration column overhead stream 91 that is passed through a condenser to form reflux stream 94 and wet ethanol stream 92 that is then sent to molecular sieve 80 inlet. Ethyl acetate column 60 bottoms stream 65 comprising wet ethanol is also sent to molecular sieve 80 inlet. Ethyl acetate column bottoms stream 65 and wet ethanol stream 92 are processed in molecular sieves 80 to form water rich stream 88 and dry ethanol stream 85 wherein stream 85 is characterized by the essential absence of acetaldehyde and very low water content. Dry ethanol stream 85 is combined with splitter column second overhead stream 54 comprising ethanol and acetaldehyde to form mixed ethanol feed stream 35. Mixed alcohol feed stream 35 is combined with gas stream 33 comprising hydrogen to form reactor feed stream 36. Reactor feed stream 36 is heated to form reactor feed stream 37 that is sent to reactor system 40 containing one reactor, or two or more reactors. In reactor system 40, ethanol is contacted with a Guerbet catalyst under elevated pressure and temperature conditions to form n-butanol reactor product stream 45. n-butanol reactor product stream 45 is processed in splitter column 50 to form splitter column bottoms stream 58 predominantly comprising high boiling compounds including n-butanol, i-butanol, hexanol and octanol and splitter column first overhead stream 51 comprising ethanol, acetaldehyde, ethyl acetate, hydrogen and carbon monoxide. Splitter column first overhead stream 51 is passed through a condenser to form (i) first condensate stream 52 that is divided between splitter column 50 reflux and ethyl acetate column 60 feed and (ii) splitter column first gas stream 53. Splitter column gas stream 53 is passed through a second condenser to form splitter column second overhead condensate stream 54 and splitter column second gas stream 55. Splitter column second gas stream 55 is pressurized in recycle compressor 20 to form compressed splitter column second gas stream 21 that may be the gas source for gas stream 33. In some other aspects of the present invention, compressed splitter column second gas stream 21 may be processed by pressure swing adsorption 30 to form hydrogen gas stream 32 that is the gas source for gas stream 33 and purge stream 31 comprising hydrogen, carbon dioxide, carbon monoxide and ethane. In some other aspects of the present invention, a combination of compressed splitter column second gas stream 21 and hydrogen gas stream 32 form gas stream 33. In some further aspects of the present invention not depicted in FIG. 1, at least a portion of the hydrogen present in the reaction mixture is provided by a source of fresh hydrogen make-up. At least a portion of splitter column first condensate stream 52 is forwarded to ethyl acetate column 60 where it is processed to form ethyl acetate column bottoms stream 65 and ethyl acetate column overhead stream 61. Ethyl acetate column overhead stream 61 is passed through a condenser to form ethyl acetate column overhead gas purge stream 62 comprising acetaldehyde, hydrogen and ethyl acetate as major components and ethyl acetate column overhead condensate stream 63 comprising acetaldehyde, ethanol and ethyl acetate as major components. A portion of stream 63 is recycled to ethyl acetate column 60 and a portion of stream 63 is purged from the process. In one optional aspect of the present invention, stream 63 may be purified, such as by distillation column 70, to form purified ethyl acetate stream 72. Splitter column bottoms stream 58 is processed in hexanol column 100 to form hexanol column bottoms stream 105 comprising hexanol and octanol as major components and hexanol column condense overhead stream 106 comprising n-butanol and minor amounts of n-propanol, i-butanol and 2-butanol. Hexanol column condense overhead stream 106 is processed in isobutanol column 110 to form a hexanol column bottoms stream 115 comprising essentially pure n-butanol and a condensed hexanol column overhead stream 116 comprising n-propanol, i-butanol, 2-butanol and n-butanol as major components.

Figure 2:
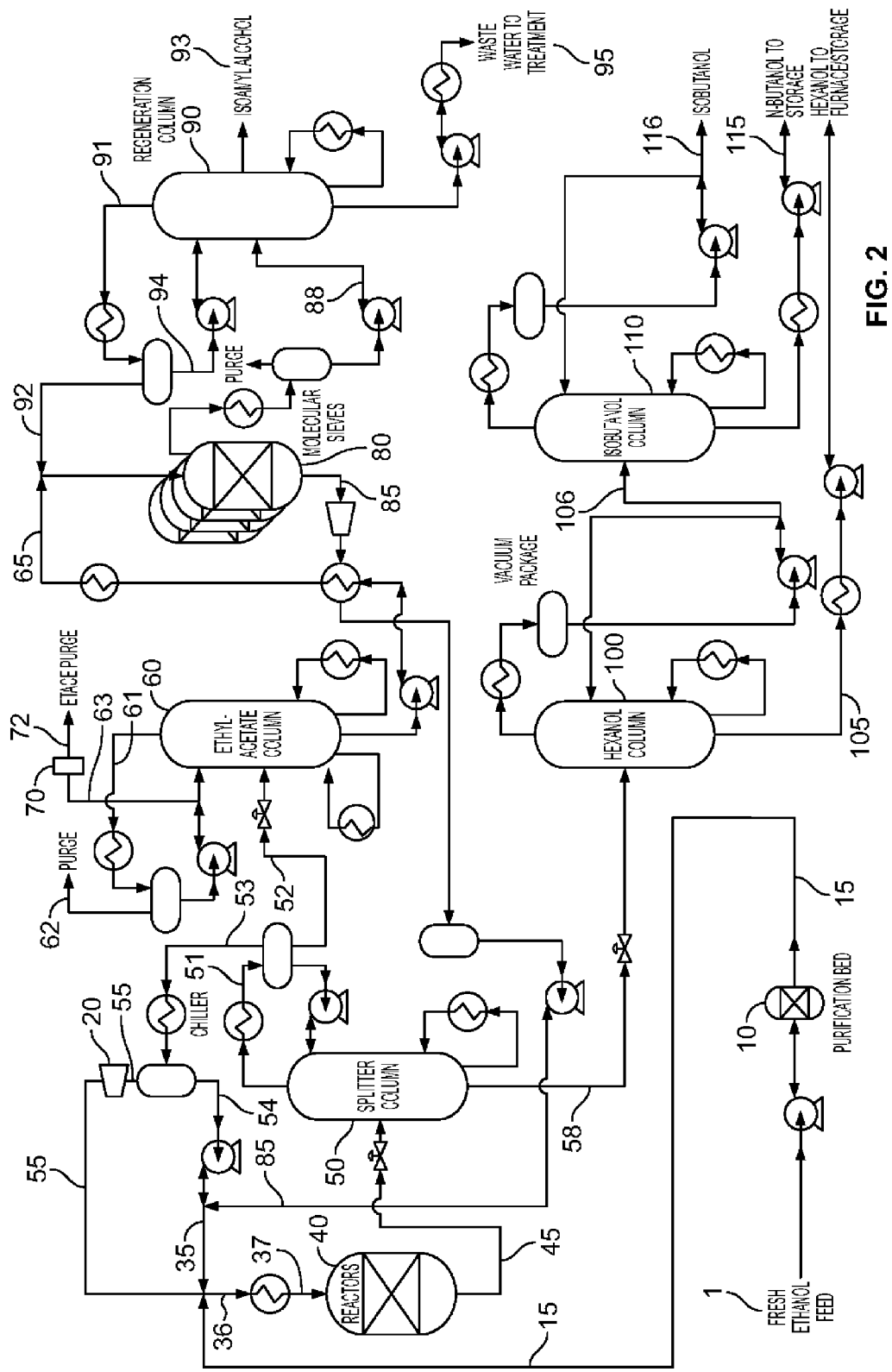
FIG. 2 is a process flow diagram of a second aspect of the present invention.
Figure 3:
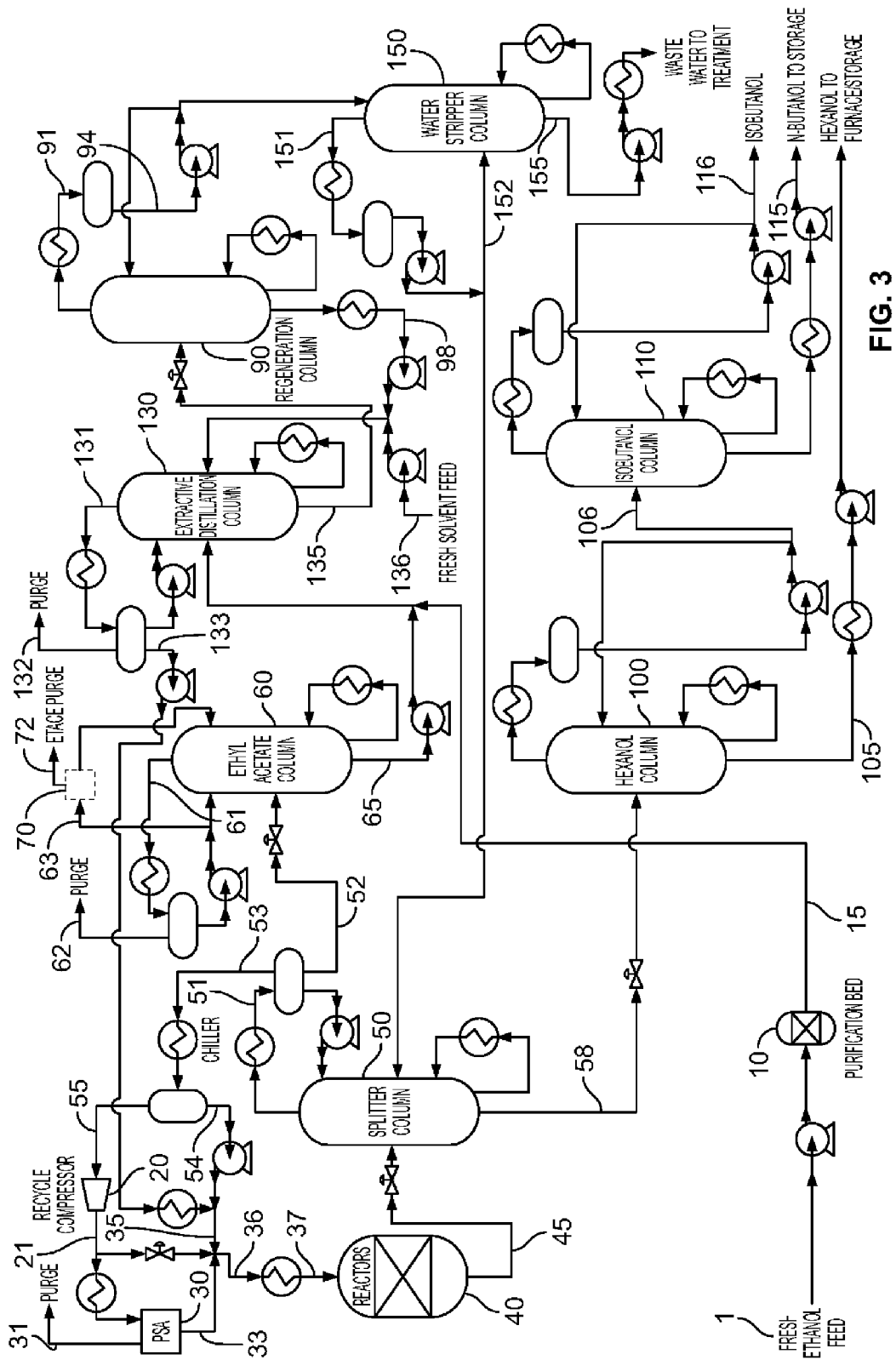
FIG. 3 is a process flow diagram of a third aspect of the present invention.

In another aspect of the present invention, depicted in FIG. 2, fresh ethanol feed 1 is optionally passed through purification bed 10 for removal of impurities (e.g., salts and ions) to form a fresh ethanol feed stream 15 comprising ethanol and water. In some aspects of the present invention, fresh ethanol may comprise isoamyl alcohol. Feed stream 15 is combined with splitter column second gas stream 55 comprising hydrogen (described below) and recovered ethanol feed stream 35 (described below) to form reactor feed stream 36. Reactor feed stream 36 is heated to form reactor feed stream 37 that is sent to reactor system 40 containing one reactor, or two or more reactors. In reactor system 40, ethanol is contacted with a Guerbet catalyst under elevated pressure and temperature conditions to form n-butanol reactor product stream 45. n-butanol reactor product stream 45 is processed in splitter column 50 to form splitter column bottoms stream 58 predominantly comprising high boiling compounds including n-butanol, i-butanol, hexanol and octanol and splitter column first overhead stream 51 comprising low boiling compounds including ethanol, acetaldehyde, ethyl acetate, hydrogen and carbon monoxide. Splitter column first overhead stream 51 is passed through a condenser to form (i) first condensate stream 52 that is divided between splitter column 50 reflux and ethyl acetate column 60 feed and (ii) splitter column first gas stream 53. Splitter column gas stream 53 is passed through a second condenser to form splitter column second overhead condensate stream 54 and splitter column second gas stream 55. Splitter column second gas stream 55 is pressurized in recycle compressor 20 prior to combination with fresh ethanol feed stream 15 and recovered ethanol feed stream 35. In some further aspects of the present invention not depicted in FIG. 2, at least a portion of the hydrogen present in the reaction mixture is provided by a source of fresh hydrogen make-up. At least a portion of splitter column first condensate stream 52 is forwarded to ethyl acetate column 60 where it is processed to form ethyl acetate column bottoms stream 65 and ethyl acetate column overhead stream 61. Ethyl acetate column overhead stream 61 is passed through a condenser to form ethyl acetate column overhead gas purge stream 62 comprising acetaldehyde, hydrogen and ethyl acetate as major components and ethyl acetate column overhead condensate stream 63 comprising acetaldehyde, ethanol and ethyl acetate as major components. A portion of stream 63 is recycled to ethyl acetate column 60 and a portion of stream 63 is purged from the process. In one optional aspect of the present invention, stream 63 may be purified, such as by distillation column 70, to form purified ethyl acetate stream 72. Ethyl acetate column 60 bottoms stream 65 comprising and wet recovered ethanol stream 92 are processed in molecular sieves 80 to form water rich stream 88 and dry recovered ethanol stream 85 wherein stream 85 is characterized by the essential absence of acetaldehyde and very low water content. Dry recovered ethanol stream 85 is combined with splitter column second overhead stream 54 comprising ethanol and acetaldehyde to form recovered ethanol feed stream 35. Molecular sieve 80 water rich feed stream 88 comprising ethanol is processed in regeneration column 90. Regeneration column 90 separates water and isoamyl alcohol from ethanol to form regeneration column bottoms stream 95 comprising water that is sent to waste water treatment, isoamyl alcohol stream 93 and regeneration column overhead stream 91 that is passed through a condenser to form reflux stream 94 and wet ethanol stream 92 that is then sent to molecular sieve 80 inlet. Splitter column bottoms stream 58 is processed in hexanol column 100 to form hexanol column bottoms stream 105 comprising hexanol and octanol as major components and hexanol column condenser overhead stream 106 comprising n-butanol and minor amounts of n-propanol, i-butanol and 2-butanol. Hexanol column condense overhead stream 106 is processed in isobutanol column 110 to form a isobutanol column bottoms stream 115 comprising essentially pure n-butanol and a condensed hexanol column overhead stream 116 comprising n-propanol, i-butanol, 2-butanol and n-butanol as major components In another aspect of the present invention, depicted in FIG. 3, fresh ethanol feed 1 is optionally passed through purification bed 10 for removal of impurities (e.g., salts and ions) to form a fresh ethanol feed stream 15 comprising ethanol and water. In some aspects of the present invention, fresh ethanol may comprise isoamyl alcohol. Feed stream 15 is sent to extractive distillation column 130 inlet. Ethyl acetate column bottom stream 65 (comprising ethanol and water) is also sent to extractive distillation column 130 inlet. The combined streams are contacted with an extractive solvent in extractive distillation column 130 to form extractive distillation column overhead stream 131 and bottoms stream 135. Overhead stream 131 is passed through a condenser to form dry ethanol feed stream 133 and purge stream 132. Bottoms stream 135 comprising contaminated extractive solvent is sent to regeneration column 90 to generate a bottoms stream comprising recovered extractive solvent 98 that is transferred to extractive distillation column 130. Extractive solvent make-up to extractive distillation column 130 is done via fresh extractive solvent feed 136. Regeneration column overhead stream 91 is passed through a condenser to form regeneration column condensed overhead stream 94 that is rich in water. At least a portion of stream 94 may be refluxed to column 130 and at least a portion is fed to water striper column 150 for removal of organic components therefrom as water stripper column overhead stream 151 that is passed through a condenser to form stream 152. At least a portion of stream 152 may be refluxed to water stripper column 150 and at least a portion is transferred to splitter column 50. Water stripper column bottoms stream 155 is discharged to waste water treatment. Dry ethanol feed stream 133 is combined with splitter column second overhead stream 54 comprising ethanol and acetaldehyde to form mixed ethanol feed stream 35. Mixed alcohol feed stream 35 is combined with gas stream 33 comprising hydrogen to form reactor feed stream 36. In some further aspects of the present invention not depicted in FIG. 3, at least a portion of the hydrogen present in the reaction mixture is provided by a source of fresh hydrogen make-up. Reactor feed stream 36 is heated to form reactor feed stream 37 that is sent to reactor system 40 containing or reactor, or two or more reactors. In reactor system 40, ethanol is contacted with a Guerbet catalyst under elevated pressure and temperature conditions to form n-butanol reactor product stream 45. n-butanol reactor product stream 45 is processed in splitter column 50 to form splitter column bottoms stream 58 predominantly comprising high boiling compounds including n-butanol, i-butanol, hexanol and octanol and splitter column first overhead stream 51 comprising lower boiling compounds including ethanol, acetaldehyde, ethyl acetate, hydrogen and carbon monoxide. Splitter column first overhead stream 51 is passed through a condenser to form condensate stream 52. At least a portion of condensate stream 52 may be refluxed to splitter column 50 and as least a portion is fed forward to ethyl acetate column 60 where it is processed to form ethyl acetate column bottoms stream 65 and ethyl acetate column overhead stream 61. In some optional aspects of the present invention, at least a portion of condensate stream 52 may be purged from the process. Splitter column gas stream 53 passed through a heat exchanger to form splitter column second overhead stream 54 and splitter column second gas stream 55. Splitter column second gas stream 55 is pressurized in recycle compressor 20. In some aspects of the present invention, compressed splitter column second gas stream 21 may be the gas source for gas stream 33. In some other aspects of the present invention, compressed splitter column second gas stream 21 may be processed by pressure swing adsorption 30 to form gas stream 33 and purge stream 31 comprising hydrogen, carbon dioxide, carbon monoxide and ethane. In some other aspects of the present invention, a combination of compressed splitter column second gas stream 21 and gas stream 33 are the gas source for reactors 40. Ethyl acetate column overhead stream 61 is passed through a condenser to form ethyl acetate column overhead gas purge stream 62 comprising acetaldehyde, hydrogen and ethyl acetate as major components and ethyl acetate column overhead condensate stream 63 comprising acetaldehyde, ethanol and ethyl acetate as major components. A portion of stream 63 is recycled to ethyl acetate column 60 and a portion of stream 63 is purged from the process. In one optional aspect of the present invention, stream 63 may be purified, such as by distillation column 70, to form purified ethyl acetate stream 72. Splitter column bottoms stream 58 is processed in hexanol column 100 to form hexanol column bottoms stream 105 comprising hexanol and octanol as major components and hexanol column overhead stream 106 comprising n-butanol and minor amounts of n-propanol, i-butanol and 2-butanol. Hexanol column overhead stream 106 is processed in isobutanol column 110 to form a isobutanol column bottoms stream 115 comprising essentially pure n-butanol and a condensed isobutanol column overhead stream 116 comprising n-propanol, i-butanol, 2-butanol and n-butanol as major components.

Figure 4:
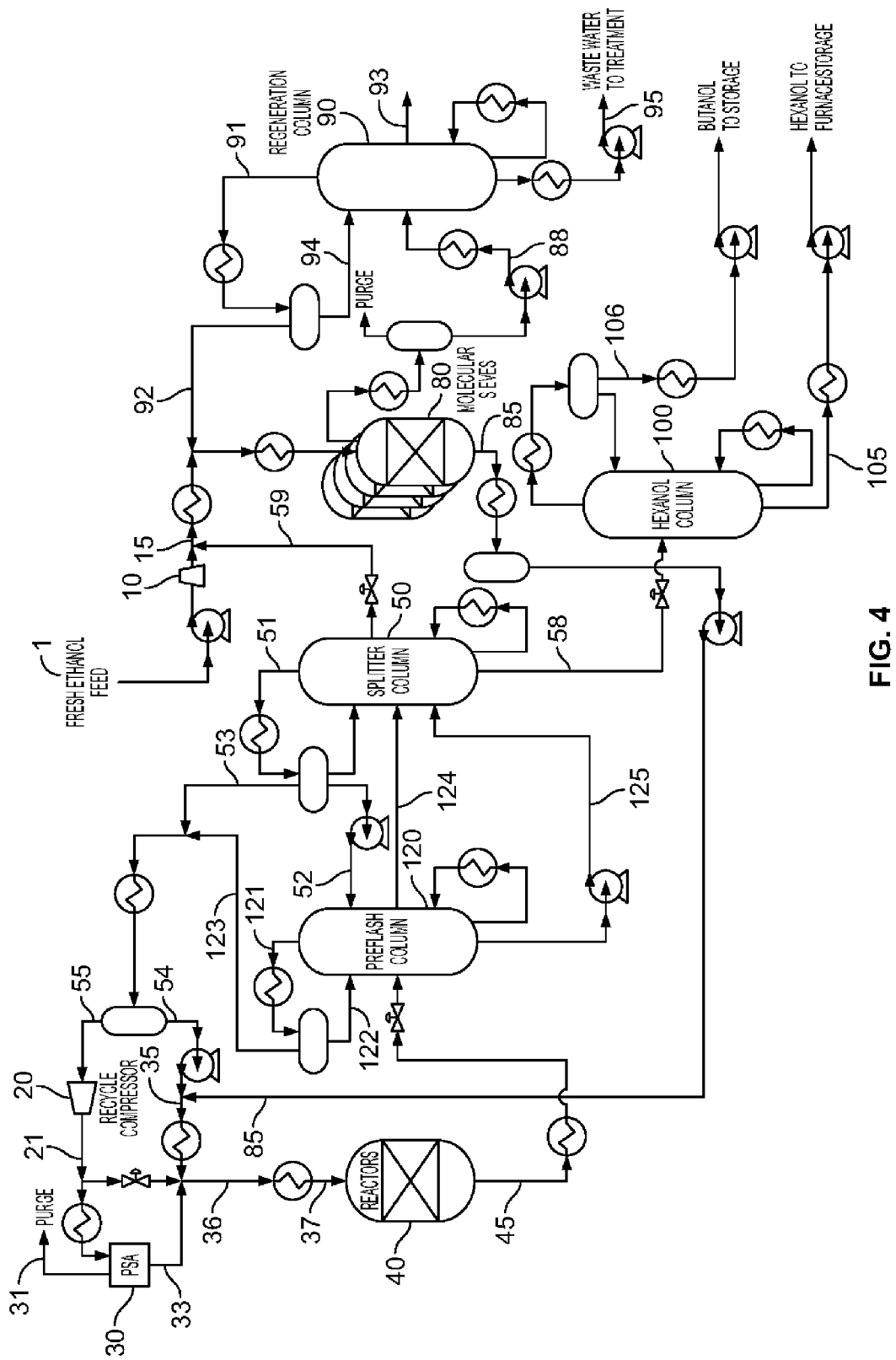
FIG. 4 is a process flow diagram of a fourth aspect of the present invention.

In another aspect of the present invention, depicted in FIG. 4, fresh ethanol feed 1 is optionally passed through purification bed 10 for removal of impurities (e.g., salts and ions) to form a fresh ethanol feed stream 15 comprising ethanol and water. In some aspects of the present invention, fresh ethanol may comprise isoamyl alcohol. Feed stream 15 is sent to molecular sieve 80 inlet. Splitter column 50 intermediate stream 59 (comprising ethanol and water) and regeneration column 90 wet ethanol stream 92 are also sent to molecular sieve 80 inlet. The combined streams are processed in molecular sieves 80 to form water rich feed stream 88 and dry ethanol stream 85. Molecular sieve water rich feed stream 88 is processed in regeneration 90 for the separation of water and isoamyl alcohol from ethanol to form regeneration column bottoms stream 95 comprising water that is sent to waste water treatment, isoamyl alcohol stream 93 and regeneration column overhead stream 91 that is passed through a condenser to form reflux stream 94 and wet ethanol stream 92 that is then sent to molecular sieve 80 inlet. Dry ethanol stream 85 is combined with splitter column second overhead stream 54 comprising ethanol and acetaldehyde to form mixed ethanol feed stream 35. Mixed alcohol feed stream 35 is combined with gas stream 33 comprising hydrogen to form reactor feed stream 36. In some further aspects of the present invention not depicted in FIG. 4, at least a portion of the hydrogen present in the reaction mixture is provided by a source of fresh hydrogen make-up. Reactor feed stream 36 is heated to form reactor feed stream 37 that is sent to reactor system 40 containing one reactor, or two or more reactors. In reactor system 40, ethanol is contacted with a Guerbet catalyst under elevated pressure and temperature conditions to form n-butanol reactor product stream 45. n-butanol reactor product stream 45 is processed in preflash column 120 to form preflash column bottoms stream 125, preflash column mid-cut stream 124 and preflash column overhead stream 121. Preflash column overhead stream 121 is passed through a condenser to form a condensate stream 122 and preflash column gas stream 123. In some aspects of the present invention not depicted in FIG. 4, at least a portion of preflash column condensate stream 122 and/or gas stream 123 may be purged from the process. Preflash column bottoms stream 125 and mid-cut stream 124 are sent to splitter column 50 to form splitter column bottoms stream 58 predominantly comprising high boiling compounds including n-butanol, i-butanol, hexanol and octanol, splitter column mid-cut stream 59 comprising ethanol and water, and splitter column first overhead stream 51 comprising lower boiling compounds including ethanol, acetaldehyde, ethyl acetate, hydrogen and carbon monoxide. Splitter column first overhead stream 51 is passed through a condenser to form condensate stream 52 that is recycled to preflash column 120 and/or to splitter column 50. In some optional aspects of the present invention, at least a portion of condensate stream 52 may be purged from the process. Splitter column gas stream 53 is combined with preflash column gas stream 123 and further condensed to form splitter column second overhead stream 54 and splitter column second gas stream 55. Splitter column second gas stream 55 is pressurized in recycle compressor 20. In some aspects of the present invention, compressed splitter column second gas stream 21 may be the gas source for gas stream 33. In some other aspects of the present invention, compressed splitter column second gas stream 21 may be processed by pressure swing adsorption 30 to form gas stream 33 and purge stream 31 comprising hydrogen, carbon dioxide, carbon monoxide and ethane. In some other aspects of the present invention, a combination of compressed splitter column second gas stream 21 and gas stream 33 are the gas source for reactors 40. Splitter column bottoms stream 58 is processed in hexanol column 100 to form hexanol column bottoms stream 105 comprising hexanol and octanol as major components and hexanol column condensed overhead stream 106 comprising n-butanol and minor amounts of n-propanol, i-butanol and 2-butanol. Optionally, and not depicted in FIG. 4, hexanol column condense overhead stream 106 may be processed in an isobutanol column to form a hexanol column bottoms stream comprising essentially pure n-butanol and a condensed hexanol column overhead stream comprising n-propanol, i-butanol, 2-butanol and n-butanol as major components.

Figure 5:
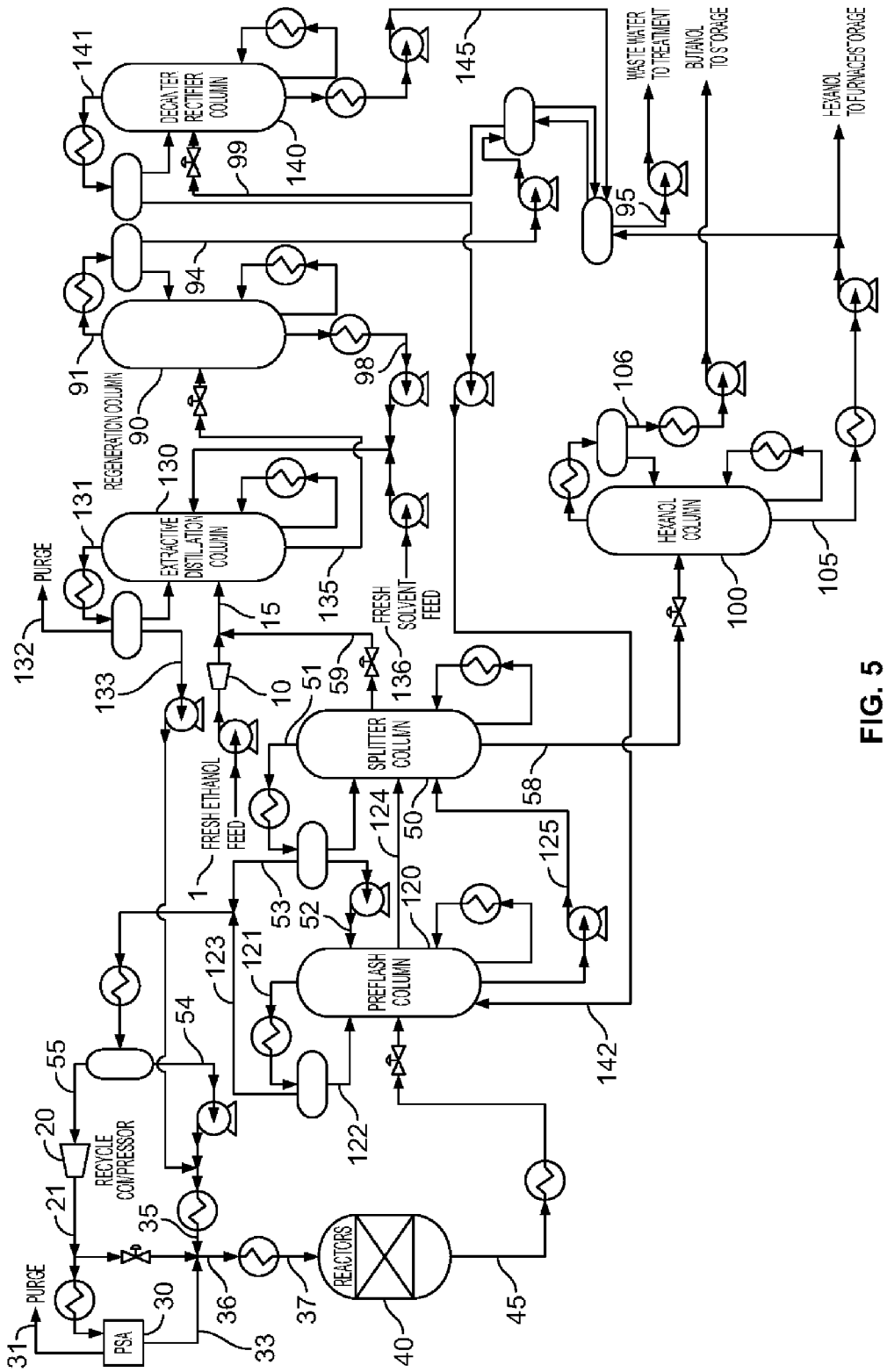
FIG. 5 is a process flow diagram of a fifth aspect of the present invention.

In another aspect of the present invention, depicted in FIG. 5, fresh ethanol feed 1 is optionally passed through purification bed 10 for removal of impurities (e.g., salts and ions) to form a fresh ethanol feed stream 15 comprising ethanol and water. In some aspects of the present invention, fresh ethanol may comprise isoamyl alcohol. Feed stream 15 is sent to extractive distillation column 130 inlet. Splitter column intermediate stream 59 (comprising ethanol and water) is also sent to extractive distillation column 130 inlet. The combined streams are contacted with an extractive solvent in extractive distillation column 130 to form extractive distillation column overhead stream 131 and bottoms stream 135. Overhead stream 131 is passed through a condenser to form dry ethanol feed stream 133 and purge stream 132. Bottoms stream 135 comprising contaminated extractive solvent is sent to regeneration column 90 to generate a bottoms stream comprising recovered extractive solvent 98 that is transferred to extractive distillation column 130. Extractive solvent make-up to extractive distillation column 130 is done via fresh solvent feed 136. Column overhead stream 91 is passed through a condenser to form regeneration column condensed overhead stream 94 that is rich in water. At least a portion of stream 94 may be refluxed to column 90 and at least a portion may be discharged to waste water treatment 95. Decanter rectifier column 140 receives various streams containing organic components including regeneration column condensed overhead stream 94, hexanol column bottoms stream 105, and decanter rectifier column bottoms stream 145, depicted as combined stream 99, and strips organic components therefrom as decanter rectifier overhead stream 141 that is passed through a condenser and recycled to preflash column 120 as stream 142. At least a portion of rectifier column bottoms stream 145 is discharged to waste water treatment 95. Dry ethanol feed stream 133 is combined with splitter column second overhead stream 54 comprising ethanol and acetaldehyde to form mixed ethanol feed stream 35. Mixed alcohol feed stream 35 is combined with gas stream 33 comprising hydrogen to form reactor feed stream 36. In some further aspects of the present invention not depicted in FIG. 5, at least a portion of the hydrogen present in the reaction mixture is provided by a source of fresh hydrogen make-up. Reactor feed stream 36 is heated to form reactor feed stream 37 that is sent to reactor system 40 containing one reactor, or two or more reactors. In reactor system 40, ethanol is contacted with a Guerbet catalyst under elevated pressure and temperature conditions to form n-butanol reactor product stream 45. n-butanol reactor product stream 45 is processed in preflash column 120 to form preflash column bottoms stream 125, preflash column mid-cut stream 124 and preflash column overhead stream 121. Preflash column overhead stream 121 is passed through a condenser to form a condensate stream 122 and preflash column gas stream 123. In some aspects of the present invention not depicted in FIG. 5, at least a portion of preflash column condensate stream 122 and/or gas stream 123 may be purged from the process. Preflash column bottoms stream 125 and mid-cut stream 124 are sent to splitter column 50 to form splitter column bottoms stream 58 predominantly comprising high boiling compounds including n-butanol, i-butanol, hexanol and octanol, splitter column mid-cut stream 59 comprising ethanol and water, and splitter column first overhead stream 51 comprising lower boiling compounds including ethanol, acetaldehyde, ethyl acetate, hydrogen and carbon monoxide. Splitter column first overhead stream 51 is passed through a condenser to form condensate stream 52 that is recycled to preflash column 120 and/or to splitter column 50. In some optional aspects of the present invention, at least a portion of condensate stream 52 may be purged from the process. Splitter column gas stream 53 is combined with preflash column gas stream 123 and further condensed to form splitter column second overhead stream 54 and splitter column second gas stream 55. Splitter column second gas stream 55 is pressurized in recycle compressor 20. In some aspects of the present invention, compressed splitter column second gas stream 21 may be the gas source for gas stream 33. In some other aspects of the present invention, compressed splitter column second gas stream 21 may be processed by pressure swing adsorption 30 to form gas stream 33 and purge stream 31 comprising hydrogen, carbon dioxide, carbon monoxide and ethane. In some other aspects of the present invention, a combination of compressed splitter column second gas stream 21 and gas stream 33 are the gas source for reactors 40. Splitter column bottoms stream 58 is processed in hexanol column 100 to form hexanol column bottoms stream 105 comprising hexanol and octanol as major components and hexanol column condensed overhead stream 106 comprising n-butanol and minor amounts of n-propanol, i-butanol and 2-butanol. Optionally, and not depicted in FIG. 5, hexanol column condense overhead stream 106 may be processed in an isobutanol column to form a hexanol column bottoms stream comprising essentially pure n-butanol and a condensed hexanol column overhead stream comprising n-propanol, i-butanol, 2-butanol and n-butanol as major components.

Figure 6:
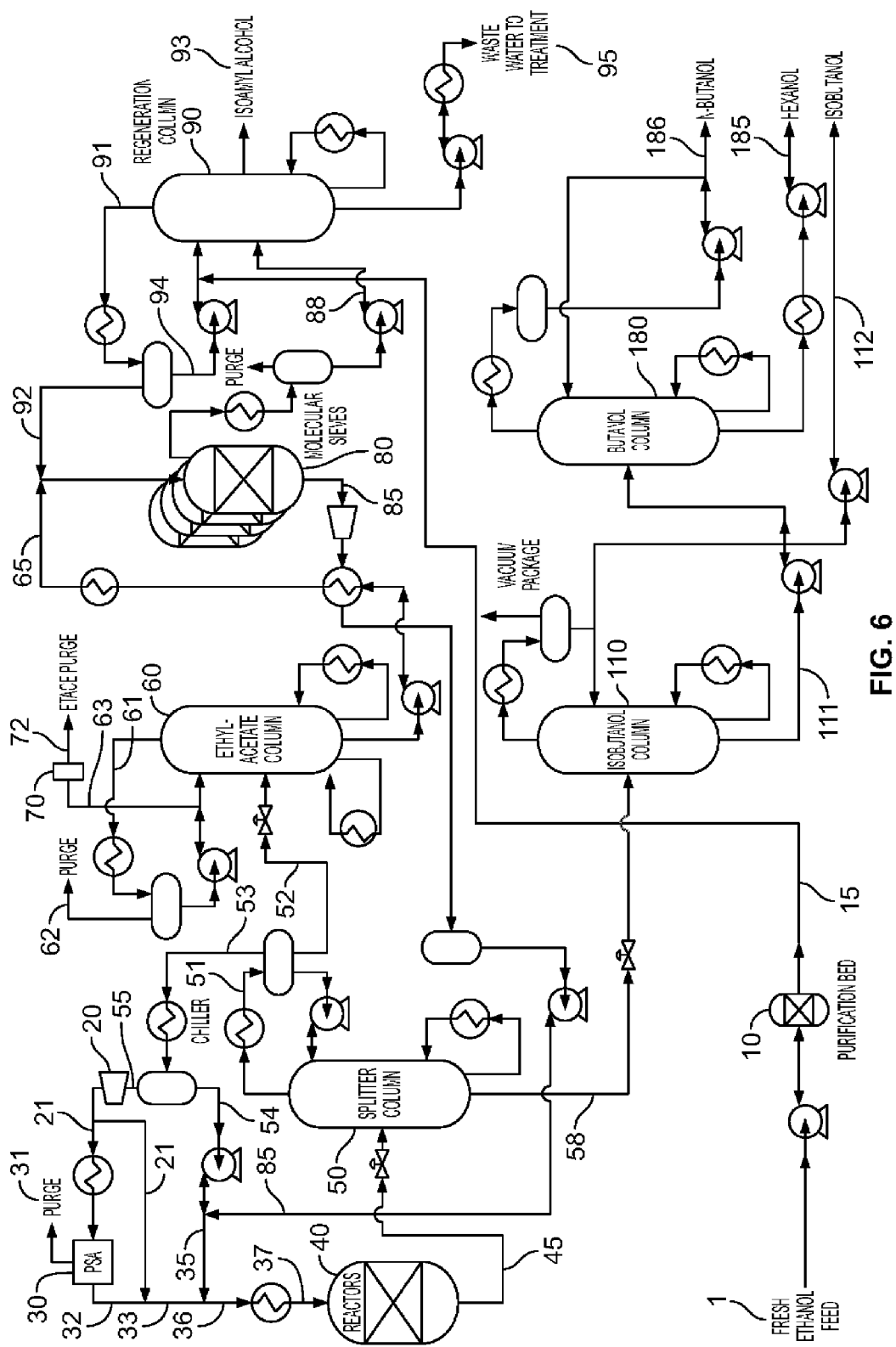
FIG. 6 is a process flow diagram of a sixth aspect of the present invention.

In another aspect of the present invention, depicted in FIG. 6, splitter column bottoms stream 58 may be processed in an alternate fractionation aspect to form n-butanol, i-butanol and hexanol streams. Although FIG. 6 is depicted in reference to the process arrangement of FIG. 1, the FIG. 6 fractionation aspect of the present invention can be applied to any aspect of the present invention for the fractionation of a process stream comprising n-butanol, i-butanol and hexanol, such as the aspects of the present invention depicted in FIGS. 2 to 5. In the FIG. 6 fractionation aspect of the present invention, splitter column bottoms stream 58 is processed in isobutanol column 110 to form isobutanol column bottoms stream 111 comprising n-butanol and hexanol as major components and isobutanol column condenser overhead stream 112 predominantly comprising i-butanol. At least a portion of isobutanol column condenser overhead stream 112 may be refluxed to isobutanol column 110 and at least a portion may be purged from the process. Isobutanol column bottoms stream 111 is processed in butanol column 180 to form a butanol column bottoms stream 185 predominantly comprising hexanol and a butanol column overhead stream 186 comprising essentially pure n-butanol. At least a portion of butanol column overhead stream 186 may be refluxed to butanol column 180.

Figure 7:
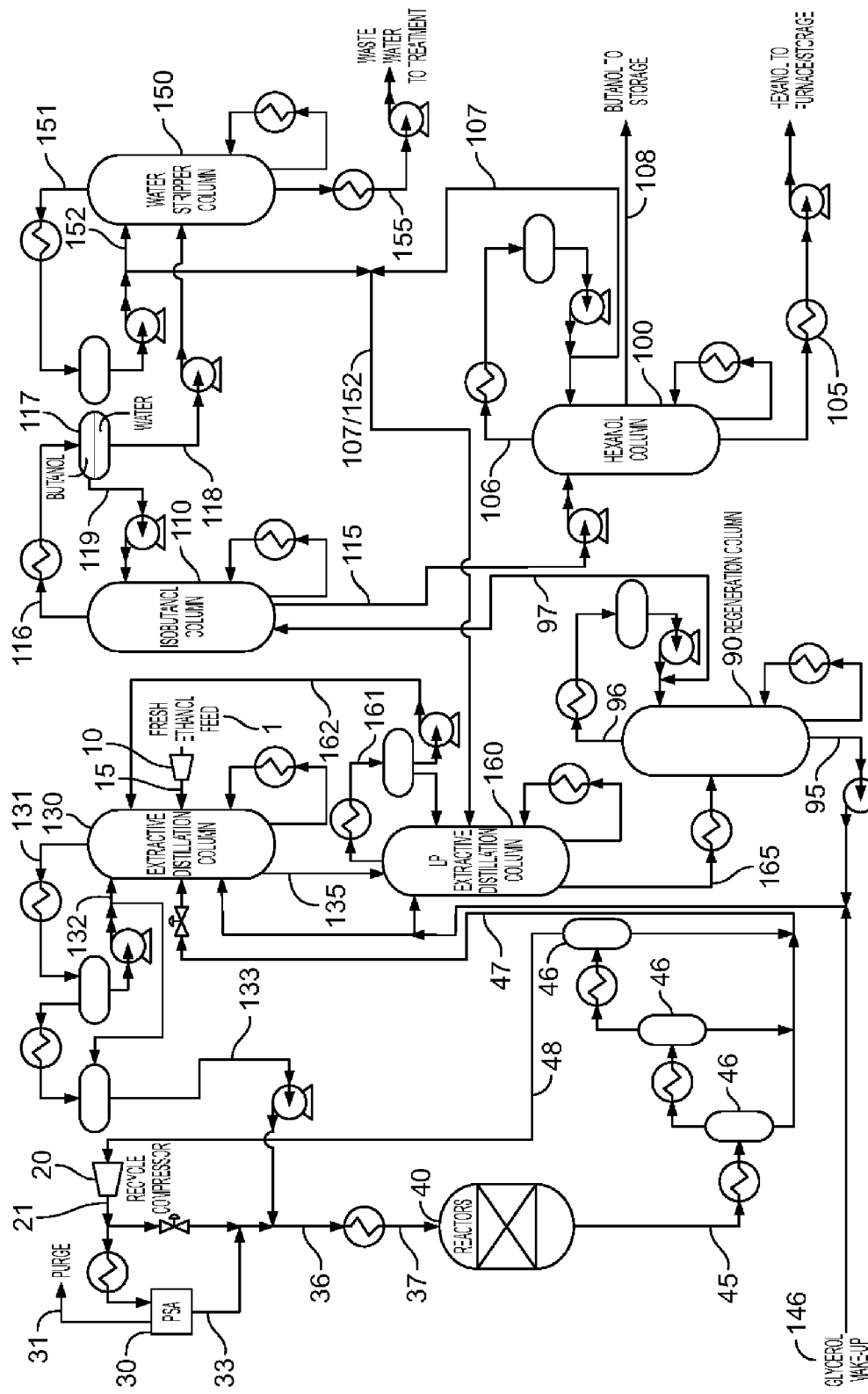
FIG. 7 is a process flow diagram of a seventh aspect of the present invention.

In another aspect of the present invention, depicted in FIG. 7, fresh ethanol feed 1 is optionally passed through purification bed 10 for removal of impurities (e.g., salts and ions) to form a fresh ethanol feed stream 15 comprising ethanol and water. In some aspects of the present invention, fresh ethanol further comprises isoamyl alcohol. Feed stream 15 is sent to extractive distillation column 130 inlet. Reactor condensate stream 47 and extractive distillation column overhead stream 162 are also fed to extractive distillation column 130. The combined streams are contacted with glycerol in extractive distillation column 130 at a higher pressure than the pressure used in low pressure extractive distillation column 160 to form extractive distillation column overhead stream 131 and bottoms stream 135. For instance, the pressure in extractive distillation column 130 may be at least about 3 bara higher than pressure in low pressure extractive distillation column 160. Overhead stream 131 is passed through a first condenser to form extractive distillation column condensate stream 132 and a gas stream. FIG. 7 depicts passing the gas stream through a second condenser to form an extractive distillation column second condensate stream 133. Condensate stream 132 may optionally refluxed to extractive distillation column 130 and/or be combined with second extractive distillation column condensate stream 133. Although not depicted in FIG. 7, one or more gas purge and/or liquid purge streams may be present in the extractive distillation column 130 overhead system to purge ethyl acetate and acetaldehyde from the process. Extractive distillation column second condensate stream 133 comprises essentially pure dry ethanol and is the ethanol feedstock for reactor 40. n-butanol reactor product stream 45 generated in reactor 40 may be passed through one or more condensers and fed forward to separation tank system 46 to form gas stream 48 comprising hydrogen, water, carbon dioxide, carbon monoxide and acetaldehyde and condensate stream 47 comprising n-butanol, ethanol, water, acetaldehyde and ethyl acetate. Gas stream 48 is pressurized in recycle compressor 20 to form compressed splitter column second gas stream 21. In some aspects of the present invention, compressed splitter column second gas stream 21 may be the gas source for gas stream 33. In some other aspects of the present invention, compressed splitter column second gas stream 21 may be processed by pressure swing adsorption 30 to form gas stream 33 and purge stream 31 comprising hydrogen, carbon dioxide, carbon monoxide and methane. In some other aspects of the present invention, a combination of compressed splitter column second gas stream 21 and gas stream 33 are the gas source for reactors 40. Extractive distillation column second condensate stream 133 is combined with gas stream 33 comprising hydrogen to form reactor feed stream 36. In some further aspects of the present invention not depicted in FIG. 7, at least a portion of the hydrogen present in the reaction mixture is provided by a source of fresh hydrogen make-up. Reactor feed stream 36 is heated and pressurized to form reactor feed stream 37 that is sent to reactor system 40 containing one reactor, or two or more reactors. In reactor system 40, ethanol is contacted with a Guerbet catalyst under elevated pressure and temperature conditions to form n-butanol reactor product stream 45. Extractive distillation column 130 bottoms stream 135 comprising glycerol and n-butanol is fed to low pressure extractive distillation column 160 where the mixture is subjected to a second, lower pressure, distillation. Overhead stream 161 is passed through a condenser to form stream 162 that is refluxed to low pressure extractive distillation column 160 and/or refluxed to extractive distillation column 130. Low pressure extractive distillation column bottoms 165 are fed to regeneration column 90 where organic materials are stripped into overhead steam 96 and glycerol is recovered in bottoms stream 95. Bottoms stream 95 is recycled to extractive distillation columns 130 and/or 160 and fresh glycerol make-up 146 is added as required. Regeneration column overhead stream 96 is passed through a condenser to form regeneration column overhead condensate stream 97 comprising n-butanol, hexanol and water. At least a portion of condensate stream 97 may be refluxed to regeneration column 90 and at least a portion is fed to isobutanol column 110. In isobutanol column 110, overhead stream 116 is formed comprising an azeotrope of butanol and water that is collected in separation vessel 117 as butanol phase 119 and water phase 118. Butanol phase 119 is refluxed to isobutanol column 110 and water phase 118 is fed to water stripper column 150. Organic compounds are stripped from water phase 118 to form overhead stream 151 that is passed through a condenser to form overhead stream 152. At least a portion of overhead stream 152 is refluxed to water stripper column 150 and at least a portion is fed to low pressure extractive distillation column 160. Extractive distillation bottoms stream 155 is processed in waste water treatment. Isobutanol column bottoms stream 115 is fed to hexanol column 100 for the separation of butanol from hexanol. In hexanol column 100, bottoms stream 105 comprising hexanol and intermediate cut stream 108 comprising essentially pure butanol are formed. An overhead stream 106 is formed comprising water and low boiling organic compounds that is passed through a condenser to form overhead stream 107. Overhead stream 107 may be fed to low pressure extractive distillation column 160 and/or to water stripper column 150.

Figure 8:
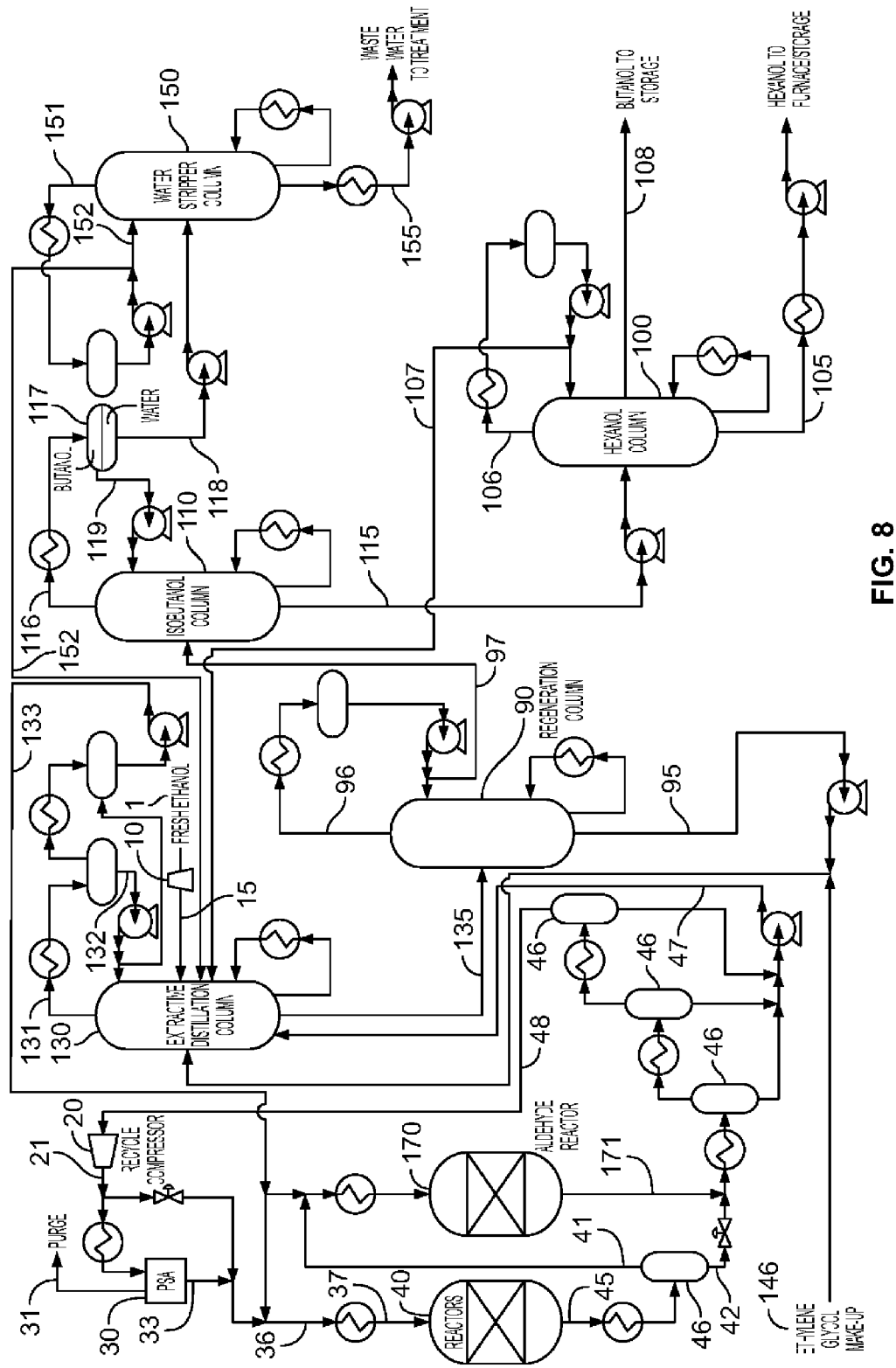
FIG. 8 is a process flow diagram of an eighth aspect of the present invention.

In another aspect of the present invention, depicted in FIG. 8, fresh ethanol feed 1 is optionally passed through purification bed 10 for removal of impurities (e.g., salts and ions) to form a fresh ethanol feed stream 15 comprising ethanol and water. In some aspects of the present invention, fresh ethanol may comprises isoamyl alcohol. Feed stream 15 is sent to extractive distillation column 130 inlet. Water stripper column overhead stream 152 and hexanol column overhead stream 107 are also fed to extractive distillation column 130. The combined streams are contacted with ethylene glycol in extractive distillation column 130 to form extractive distillation column overhead stream 131 and bottoms stream 135. Overhead stream 131 is passed through a first condenser to form extractive distillation column condensate stream 132 and a gas stream. FIG. 8 depicts passing the gas stream through a second condenser to form an extractive distillation column second condensate stream 133. Condensate stream 132 may optionally refluxed to extractive distillation column 130 and/or be combined with second extractive distillation column condensate stream 133. Although not depicted in FIG. 8, one or more gas purge and/or liquid purge streams may be present in the extractive distillation column 130 overhead system to purge ethyl acetate and acetaldehyde from the process. Extractive distillation column second condensate stream 133 comprises ethanol and acetaldehyde, and is the ethanol feedstock for reactor 40. n-butanol reactor product stream 45 generated in reactor 40 is passed through a condenser and fed forward to separation tank 46 to form gas stream 41 that passes through aldehyde reactor 170 to form stream 171 that is combined with condensed stream 42 (if present). Combined streams 171 and 42 (optionally) pass through one or more condensers and separation tank system 46 to form gas stream 48 comprising hydrogen, carbon dioxide, carbon monoxide and ethanol and condensate stream 47. Gas stream 48 is pressurized in recycle compressor 20 to form compressed splitter column second gas stream 21. In some aspects of the present invention, compressed splitter column second gas stream 21 may be the gas source for gas stream 33. In some other aspects of the present invention, compressed splitter column second gas stream 21 may be processed by pressure swing adsorption 30 to form gas stream 33 and purge stream 31 comprising hydrogen, carbon dioxide, carbon monoxide and methane. In some further aspects of the present invention not depicted in FIG. 8, at least a portion of the hydrogen present in the reaction mixture is provided by a source of fresh hydrogen make-up. In some other aspects of the present invention, a combination of compressed splitter column second gas stream 21 and gas stream 33 are the gas source for reactors 40. Extractive distillation column second condensate stream 133 is combined with gas stream 33 comprising hydrogen to form reactor feed stream 36. Reactor feed stream 36 is heated and pressurized to form reactor feed stream 37 that is sent to reactor system 40 containing one reactor, or two or more reactors. In reactor system 40, ethanol is contacted with a Guerbet catalyst under elevated pressure and temperature conditions to form n-butanol reactor product stream 45. Condensate stream 47 is fed to extractive distillation column 130 to form bottoms stream 135 comprising ethylene glycol and n-butanol that is fed to regeneration column 90 where organic materials are stripped into overhead steam 96 and ethylene glycol is recovered in bottoms stream 95. Bottoms stream 95 is recycled to extractive distillation column 130 and fresh ethylene glycol make-up 146 is added as required. Regeneration column overhead stream 96 is passed through a condenser to form regeneration column overhead condensate stream 97 comprising n-butanol, hexanol and water. At least a portion of condensate stream 97 may be refluxed to regeneration column 90 and at least a portion is fed to isobutanol column 110. In isobutanol column 110, overhead stream 116 is formed comprising an azeotrope of butanol and water that is collected in separation vessel 117 as butanol phase 119 and water phase 118. Butanol phase 119 is refluxed to isobutanol column 110 and water phase 118 is fed to water stripper column 150. Organic compounds are stripped from water phase 118 to form overhead stream 151 that is passed through a condenser to form overhead stream 152. At least a portion of overhead stream 152 is refluxed to water stripper column 150 and at least a portion is fed to extractive distillation column 130. Isobutanol column bottoms stream 115 is fed to hexanol column 100 where bottoms stream 105 comprising hexanol and intermediate cut stream 108 comprising essentially pure butanol are formed. An overhead stream 106 is formed comprising water and low boiling organic compounds that is passed through a condenser to form overhead stream 107. Overhead stream 107 may be fed to extractive distillation column 130 and/or to water stripper column 150 (not depicted in FIG. 8).

In some optional aspects of the present invention not depicted in the Figures, second overhead condensate stream 54 may be optional partially or totally refluxed to ethyl acetate column 60 (FIG. 1 to 3 or 6) or to splitter column 50 (FIGS. 4 and 5). In some such aspects, such as upon start-up, second overhead condensate stream 54 may be partially or totally refluxed to ethyl acetate column 60 or splitter column 50 until steady state conditions are achieved. In some other aspects, at least a portion of stream 54 may be refluxed to column 60 or column 50 in order to control the ethyl acetate, water and/or acetaldehyde content in reactor feed stream 37. Selection of a suitable ratio of reflux to feed forward is within the purview of those skilled in the art.

In some other optional aspects of the present invention not depicted in FIGS. 1 to 8, recycle compressor 20 may be located and positioned such that reactor feed stream 37 or 38, and not splitter column second gas stream 55 or gas stream 21 is compressed and pressurized.

The process of the present invention, such as depicted in FIGS. 1 to 8, may be practiced on a continuous basis. However, the present invention is not limited to continuous processes and can be practiced on batch or semi-batch, or discontinuous processes.

Many Guerbet catalysts are known in the art. Homogeneous and heterogeneous catalysts are within the scope of the present invention. Such catalysts include alkali metal alkoxides, such as sodium ethoxide (NaOEt) (M. Guerbet, Compt. Rend. 128, 511 (1899) 1002); copper bronze (C. Weizmann, et al., J. Org. Chem 15 (1950) 54); a mixture of potassium hydroxide and boric oxide (M. Sulzbacher, J. Appl. Chem 5 (1955) 637); a mixture of magnesium oxide, carbonate potassium and copper chromite (M. N. Dvornikoff, et al., J. Org. Chem 22 (1957) 540); CaO, MgO and $Na_2CO_3$/CuO (M. N. Dvornikoff, et al., J. Org. Chem 22 (1957) 540); Ni-Raney, $MnCrO_2$, CuOx and $Zn/CrO_2$ (M. N. Dvornikoff, et al., J. Org. Chem 22 (1957) 540); an alkali metal alcoholate/boric acid ester (U.S. Pat. No. 2,861,110 (1958)); the addition of a nickel catalyst to metal alkoxide (J. Am Chem Soc 76 (1953) 52); and sodium alkoxide mixed with 5 wt. % Rh on alumina (P. L. Burk, et al., J. Mol. Catal. 33 (1985) 15). Some other Guerbet catalysts include cation exchanged zeolites, such as Metal-L (where Metal=K, Na, Ba, Cs, etc.) and Metal-X (where Metal=K, Na, Ba, Cs, among others) (U.S. Pat. No. 5,300,695; and C. Yang, Z. Meng, J. Catal. 142 (1993) 37). Still other Guerbet catalysts include Cu containing multiple basic oxides such as $Cu/ZnO/Al_2O_3$, $Cu—Co/ZnAl_2O_4$ and with K or Cs $Cu_zM-g_yCeO_x$ as promoters (J. G. Nunan, C. E. Bogdan, K. Klier, C. Young, R. G. Herman, J. Catal. 116 (1989) 195; U.S. Pat.

No. 5,387,570; and M. J. L. Gines, E. Church, J. Catal. 176 (1998) 155). Yet other Guerbet catalysts include Ru/Al$_2$O$_3$, Rh/Al$_2$O$_3$, Pd/Al$_2$O$_3$, Pt/Al$_2$O$_3$, Au/Al$_2$O$_3$, Ni/Al$_2$O$_3$, and Ag/Al$_2$O$_3$. Still another group of Guerbet catalysts include transition metals (e.g., Mn, Cr, Zn, Al, etc.) supported on MgO (W. Ueda, T. Kuwabara, T. Oshida, Y. Morikawa, J. Chem Soc, Chem Commun (1990) 1558, and Catal. Lett. 12 (1992) 971). Yet another group of Guerbet catalysts are based on calcium phosphate type hydroxyapatite (U.S. Pat. No. 6,323,383, U.S. 2007/0255079, and WO 2011/031928). Yet other Guerbet catalysts include a Group VIII metal with a phosphine ligand (US 2013/0116481).

Recently, hydrotalcite-based catalytic materials have been reported (WO 2009/026510 A1, U.S. 2010/0160693 and U.S. 2010/0160692). As is known in the art, hydrotalcite is of general formula Mg$_6$Al$_2$(CO$_3$)(OH)$_{16}$·4(H$_2$O). Studies performed with these mixed oxides of Mg and Al showed that the catalytic activity of these materials depends on the nature, the density and strength of surface basic sites, and, in turn, on the composition molar Mg/Al (J. I. Di Cosimo, et al., J. Catal. 178 (1998) 499; and J. I. Di Cosimo, et al., J. Catal. 190 (2000) 261). The prior art also been established that mixed oxides derived from hydrotalcites based on Cu/Mg/Al show improved catalytic activity (C. Carlini, et al., J. Mol. Catal. A: Chem 232 (2005) 13) or copper type catalyst systems chromite+mixed oxides of Mg and Al (derived from hydrotalcite precursors). Further, hydrotalcite-type materials (WO 2009/026510) as well as materials derived from hydrotalcites modified by including metal carbonates (WO 2009/026523) and ethylene diamine tetra acetates (WO 2009/026483) have been developed. Improved hydrotalcite-type catalysts further comprising Ga in combination with Pd and/or Pt have been discovered to produce high n-butanol yield because of a synergistic effect of Ga-Metal in the metal oxide. This improvement is even more pronounced in the case of catalysts containing Pd and Ga.

In some aspects of the present invention, the catalyst is a metal oxide that further comprises an M3 metal, where M3 is at least one trivalent metal (i.e., having a 3$^+$ charge) selected from the list comprising Al, La, Fe, Cr, Mn, Co and Ni.

In some aspects of the present invention, the catalyst can suitably be a partially or fully thermally decomposed hydrotalcite as described in U.S. Pat. No. 8,071,822 having the empirical formula:

$$[M^{2+}_{1-x}M^{3+}_x(OH)_2][\{M'A'\}^{n'-}\}_aA^{n-}_{(1-a)(n'/n)}]_{x/n}\cdot yH_2O$$

wherein M$^{2+}$ is divalent Mg, or a combination of divalent Mg and at least one divalent member selected from the group consisting of Zn, Ni, Pd, Pt, Co, Fe, and Cu; M$^{3+}$ is trivalent Al, or a combination of trivalent Al and at least one trivalent member selected from the group consisting of Fe and Cr; x is 0.66 to 0.1; M' is (i) one or more divalent members selected from the group consisting of Pd, Pt, Rh, Co, and Cu; or (ii) one or more trivalent members selected from the group consisting of Fe, Cr, Au, Ir, and Ru; or (iii) a mixture of one or more of said divalent members with one or more of said trivalent members; A' is the anion of ethylenediaminetetraacetic acid; n' is the absolute value of the sum of the oxidation state of M' (i.e., +2 if M' is one or more divalent members or +3 if M' is one or more trivalent members) and the oxidation state of the anion of ethylenediaminetetraacetic acid (−4) (for example, for M'A' wherein M' is Pd$^{2+}$ with an oxidation state of +2, n' is +2); provided that if M' is said mixture, then n' is calculated according to the following equation:

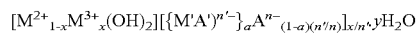
n'=the absolute value of [X$_D$(2)+X$_D$(−4)+X$_T$(3)+X$_T$(−4)], wherein wherein X$_D$=the sum of the number of moles of all divalent members divided by (the sum of the number of moles of all divalent members+the sum of the number of moles of all trivalent members), and X$_T$=the sum of the number of moles of all trivalent members divided by (the sum of the number of moles of all divalent members+the sum of the number of moles of all trivalent members); A$^{n-}$ is CO$_3^{2-}$ with n=2 or OH$^-$ with n=1; a is 0.001 to 1; and y is 0 to 4.

In a preferred embodiment, M$^{2+}$ is divalent Mg; M$^{3+}$ is trivalent Al; M' is Co or Cu; a is 0.01 to 0.44; and A$^{n-}$ is CO$_3^{2-}$ or OFF.

The catalysts described by the U.S. '822 patent are derived from a hydrotalcite of the formula as defined above by a process comprising heating the hydrotalcite for a time and at a temperature sufficient to cause a diminution in the hydrotalcite powder X-ray diffraction pattern peak intensities between 2θ angles of 10 degrees and 70 degrees using CuKα radiation.

In some other aspects of the present invention, the metal oxide is obtained from the total or partial thermal decomposition of a hydrotalcite, the catalyst having the formula [M1$_{1-(x+y)}$M2$_y$M3$_x$(OH)$_2$][A$^{m-}_{(x+y)/m}$·nH$_2$O]. In connection with this aspect, hydrotalcite is understood to mean the structural family of laminar mixed hydroxides with the formula described above. M1 is at least one bivalent metal (i.e., having a 2$^+$ charge) selected from the list comprising Mg, Zn, Cu, Co, Mn, Fe, Ni and Ca; M2 is trivalent Ga; M3 is as described above; A is at least one anion selected from the list comprising hydroxide, chloride, fluoride, bromide, iodide, nitrate, perchlorate, chlorate, bicarbonate, acetate, benzoate, methanesulfonate, ptoluenesulfonate, phenoxide, alkoxide, carbonate, sulfate, terephthalate, phosphate, hexacyanoferrate (III) and hexacyanoferrate (II); x is a value between 0 and 0.5; x is a value of from 0.1 to 0.5 or from 0.1 to 0.4; y is a value of from 0.00001 to 0.49, of from 0.00005 to 0.45 or from 0.0001 to 0.4; m is an integer of form 1 to 4; and n is greater than 0, such as from 0 to 100 or from 0 to 20; and "n" indicates the number of crystallization water molecules and is dependent on the composition of the hydrotalcite cations. In some aspects, the metal oxide is impregnated with at least one noble metal selected from the list comprising Pd, Ru, Rh and Re. The concentration of the noble metal in the metal oxide ranges between 0.001 wt. % to 10 wt. % or from 0.01 wt. % to 5 wt. % on a total metal oxide basis. In some aspects, the noble metal is Pd. In some further aspects, the impregnated metal oxide may be calcined at temperature of between about 250° C. and about 650° C. In yet further aspects, the calcined catalyst may be reduced in a hydrogen atmosphere at a temperature of between about 200° C. and about 500° C.

In some aspects of the present invention, the hydrotalcite is obtained by the co-precipitation of at least one M1 compound and at least one compound of a trivalent metal selected from the list that comprises M2 and M3. Is some other aspects, the hydrotalcite is obtained by the co-precipitation of M1, M2 and M3 compounds.

As depicted in FIGS. 1 to 8, the Guerbet reaction takes place in Reactor System 40. Reactor system 40 may comprise a single reactor or more than one reactor, such as 2, 3 or 4 reactors. Multi-reactor designs may be suitably configured in a sequential or in a parallel reactor arrangement, or a combination thereof. In some aspects of the present invention, the reaction may be carried out in at least two sequential gas phase reactors, or at least three sequential gas phase reactors. In some other aspects of the present invention, the reaction may be carried out in two or more parallel reactors. In yet other aspects, the reaction may be carried out in two or more parallel reactors and one or more reactors in sequential arrangement therewith.

The selection of suitable reactors is within the purview of those skilled in the art. Reactor designs suitable for the practice of the present invention include, for example and without limitation, discontinuous reactors, continuous stirred-tank reactors, fixed-bed continuous reactors, fluidized-bed continuous reactors, and batch reactors. Gas phase reactors having a fixed catalyst bed (containing a heterogeneous catalyst) are generally preferred. Reactors may suitably be of plug flow or turbulent flow design. The reaction conditions may be adiabatic or isothermal, or temperature gradients between reactors in multi-reactor systems may be used. In some aspects of the present invention, the reactor system comprises one or more plug flow reactors in having a fixed catalyst bed (containing a heterogeneous catalyst). In some other aspects of the present invention the reactor system can comprise at least one plug flow reactor and at least one turbulent flow reactor. The Guerbet reaction is exothermic and in some aspects of the present invention the reactors may have intercooling to allow for temperature control. Oil may be used as the reactor cooling medium, and heat may be recovered from the heated reactor cooling oil in a heat exchanger and used elsewhere in the process. In some multi-reactor aspects of the present invention, the recovered heat may be used to heat the feed stream to the first reactor.

In some aspects of the present invention, the reaction conditions and concentrations of some of the various components, and combinations of components, of the reaction mixture may be controlled in order to maximize alcohol conversion and selectivity to Guerbet alcohol reaction products.

In some aspects of the present invention, the mole ratio of hydrogen to starting alcohol in the reaction mixture may be controlled to from about 0.01:1 to about 10:1, from about 0.1:1 to about 5:1, from about 0.5:1 to about 3:1, from about 0.75:1 to about 1.5:1, from about 0.1:1 to about 0.8:1, from about 0.1:1 to about 0.6:1 or from about 0.1:1 to about 0.4:1, such as about 0.1:1, 0.2:1, 0.4:1, 0.6:1, 0.8:1, 1:1, 1.5:1, 2:1 or 3:1.

In some aspects of the present invention, the mole ratio of acetaldehyde to starting alcohol in the reactor feed stream may be controlled to from about 0.001:1 to about 0.1:1. In some other aspects of the present invention, the mole ratio of acetaldehyde to alcohol in the reactor feed stream is controlled to from about 0.001:1 to about 0.005:1 or from about 0.001:1 to about 0.003:1. In yet other aspects of the present invention, the mole ratio of acetaldehyde to alcohol in the reactor feed stream is controlled to from about 0.005:1 to about 0.05:1, from about 0.01:1 to about 0.05:1, from about 0.01:1 to about 0.04:1, or from about 0.02:1 to about 0.04:1, such as about 0.001:1, 0.002:1, 0.003:1, 0.004:1, 0.005:1, 0.01:1, 0.02:1, 0.03:1, 0.04:1 or 0.05:1.

In some aspects of the present invention, the mole ratio of water to starting alcohol in the reaction mixture may be controlled to less than about 0.005:1, less than about 0.05:1, less than about 0.025:1, from about 0.001:1 to about 0.05:1, from about 0.005:1 to about 0.05:1, or from about 0.01:1 to about 0.03:1, such as about 0.001:1, about 0.005:1, about 0.01:1, about 0.02:1 or about 0.03:1.

In some aspects of the present invention, the mole ratio of carbon monoxide to starting alcohol in the reaction mixture may be controlled to less than about 0.02:1, less than about 0.01:1, less than about 0.005:1, or less than about 0.003:1, from about 0.0005:1 to about 0.005:1, from about 0.001:1 to about 0.005:1, or from about 0.002:1 to about 0.004:1, such as about 0.005:1, about 0.003:1, about 0.002:1, or about 0.001:1.

In other aspects of the present invention, the mole ratio of ethyl acetate to starting alcohol in the reaction mixture may be controlled to less than about 0.005:1, less than about 0.002:1, or less than about 0.001:1, from about 0.0001:1 to about 0.003:1, from about 0.0005:1 to about 0.0015:1, or from about 0.0005:1 to about 0.001:1, such as about 0.0005:1, about 0.001:1, about 0.003:1 or about 0.005:1.

The Guerbet reaction mixture feed rate to the reactor is preferably controlled to provide a liquid hourly space velocity (LHSV) of from about 0.5 to about 5, from about 0.5 to about 2, from about 0.75 to about 1.5 or from about 0.9 to about 1.1, such as about 0.75, 0.9, 1, 1.1, 1.25, 1.5, 2 or 3.

Various combinations of the process variables described above may be selected to achieve high butanol yield and selectivity. For instance, the below Table A lists some possible combinations of variables (denoted by "X") that may be controlled to achieve the objects of the present invention, where "AA" refers to acetaldehyde, "CO" refers to carbon monoxide, "EA" refers to ethyl acetate, and "EtOH" refers to ethanol.

TABLE A

| | Combination | | | | | |
|---|---|---|---|---|---|---|
| | $H_2$:EtOH | AA:EtOH | $H_2O$:EtOH | CO:EtOH | EA:EtOH | LHSV |
| 1 | X | | | | | |
| 2 | | X | | | | |
| 3 | X | X | | | | |
| 4 | X | | | | X | |
| 5 | | X | | | X | |
| 6 | X | X | | | X | |
| 7 | X | | X | | | |
| 8 | | X | X | | | |
| 9 | X | X | X | | | |
| 10 | X | | | X | | |
| 11 | | X | | X | | |
| 12 | X | X | | X | | |
| 13 | X | | | | | X |
| 14 | | X | | | | X |
| 15 | X | X | | | | X |
| 16 | X | | X | X | | |
| 17 | | X | X | X | | |
| 18 | X | X | X | X | | |
| 19 | X | | X | | X | |
| 20 | | X | X | | X | |
| 21 | X | X | X | | X | |
| 22 | X | | X | X | X | |
| 23 | | X | X | X | X | |
| 24 | X | X | X | X | X | |
| 25 | X | | X | X | | X |
| 26 | | X | X | X | | X |
| 27 | X | X | X | X | | X |
| 28 | X | | X | | X | X |
| 29 | | X | X | | X | X |
| 30 | X | X | X | | X | X |
| 31 | X | | | X | X | X |
| 32 | | X | | X | X | X |
| 33 | X | X | | X | X | X |
| 34 | X | | X | X | X | X |
| 35 | | X | X | X | X | X |
| 36 | X | X | X | X | X | X |

In other aspects of the present invention, the mole ratio of alcohols other than starting alcohol to the starting alcohol (e.g., ethanol) in the reaction mixture may be controlled to from about 0.001:1 to about 0.01:1, from about 0.003:1 to about 0.01:1 or from about 0.003:1 to about 0.008:1, such as about 0.001:1, about 0.003:1, about 0.005:1, about 0.007:1 or about 0.009:1.

In some aspects of the present invention, a reactor design utilizing multiple feed points along a length of the reactor may be used to maintain a predominantly constant acetaldehyde concentration in the reaction mixture in the reagent feed section of the reactor in order to optimize n-butanol yield.

As previously disclosed, n-butanol is produced from ethanol by a two-step Guerbet reaction wherein, in the first reaction, ethanol is dehydrogenated to form acetaldehyde and hydrogen. In the second reaction, ethanol and acetaldehyde are condensed and hydrogenated to form butanol. The dehydrogenation reaction is slightly endothermic, the condensation/hydrogenation reaction is slightly exothermic, and the overall Guerbet reaction is slightly exothermic. It has been discovered that, as compared to acetaldehyde formation, acetaldehyde is rapidly condensed with ethanol to form butanol. In particular, based on a simulation as reflected in Table B below, it is believed that essentially all of the acetaldehyde present in a reaction mixture is condensed with ethanol in about the first third of the reactor length. The simulation was carried out using a kinetic model developed to represent the behavior of the catalyst under different operating conditions involving combining acetaldehyde with the ethanol and hydrogen reactor stream. The kinetic model was developed using very broad operating conditions of temperature, pressure, hydrogen to ethanol ratio and LHSV. Experimental results for the reaction of a feed stream comprising ethanol, hydrogen and acetaldehyde corresponded to, and validated, the results predicted by the kinetic model. Thus, it is believed that ethanol dehydration to acetaldehyde is the rate limiting step in the Guerbet condensation reaction.

TABLE B

| Reactor length | 1$^{st}$ Simulation (acetaldehyde mole fraction) | 2$^{nd}$ Simulation (acetaldehyde mole fraction) |
| --- | --- | --- |
| 0 cm | 0.018 | 0.037 |
| 1.1 cm | 0.006 | 0.015 |
| 2.2 cm | 0.004 | 0.006 |
| 3.3 cm | 0.003 | 0.004 |
| 4.4 cm | 0.003 | 0.003 |
| 5.5 cm | 0.003 | 0.003 |

Based on experimental evidence to date, it has been discovered that reaction of a feed stream comprising up to 0.05 moles of acetaldehyde per mole of ethanol increases n-butanol yield and selectivity. Without being bound to any particular theory, it is believed that introducing acetaldehyde with the reaction mixture overcomes the rate-limiting dehydrogenation step thereby allowing for the higher concentrations of acetaldehyde in the reaction mixture and favoring selectivity to n-butanol. It has further been discovered that reaction of a feed stream comprising in excess of about 0.05 moles of acetaldehyde per mole of ethanol (i.e., about 5 mole % acetaldehyde) reduces selectivity to n-butanol and results in increased amounts of higher alcohols as compared to feed streams comprising less than about 0.05 moles of acetaldehyde to ethanol. It is believed, without being bound by any particular theory, that reduced selectivity results from at least two factors, and combinations thereof. First, at higher acetaldehyde concentrations, the rate of aldehyde and ethanol condensation may be insufficient to consume essentially all of the acetaldehyde, thereby resulting in an acetaldehyde concentration in the reaction mixture high enough to allow for higher rates of condensation with butanol or higher alcohols as per the following example reaction schemes:

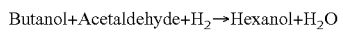

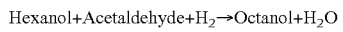

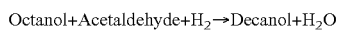

Second, it has been discovered that acetaldehyde concentrations in the feed stream in excess of about 5 or about 10 mole % causes temperature spikes, wherein higher reaction temperatures increase byproduct formation.

In accordance with the present invention, it has been discovered that a reactor feed stream comprising acetaldehyde may be fed at multiple points along the length of the reactor in order to maintain a generally constant acetaldehyde concentration in at least a portion of the reactor and thereby improve n-butanol selectivity and yield. For instance, in addition to the inlet, the reactor feed stream may be supplied at one or more injection points along the length of a portion of the reactor, termed the reactor feed section. In some aspects of the invention, the reactor feed section comprises at least a first reaction mixture addition site and a last reaction mixture addition site located along a length of the reactor, the reactor section from the first reaction mixture addition site to the last reaction mixture addition site being the reactor feed section. In some other aspects, the reactor feed section comprises at least one intermediate reaction mixture addition site located between the first reaction mixture addition site and the last reaction mixture addition site. In yet other aspects, the first reaction mixture addition site is located at the reactor inlet. In any of the various aspects, two or more injection points can be placed at intervals in the first two-thirds, first half, or first one-third of the length of the reactor. In some aspects of the present invention, the feed rate of the acetaldehyde/ethanol stream to the reactor may be based on measured acetaldehyde concentration and/or reaction temperature. Determination and selection of the reactor feed stream injection point location and profile, associated reactor feed stream addition rate, and control strategies designed to achieve an acetaldehyde concentration in the reactor feed section is within the purview of one skilled in the art.

In any of the various reactor multiple feed point aspects of the present invention, the mole ratio of acetaldehyde to ethanol in the reactor feed section may be controlled to an average of about 0.005:1, 0.01:1, 0.015:1, 0.02:1, 0.025:1, 0.03:1, 0.035:1, 0.04:1, 0.045:1 or 0.05:1, and ranges thereof, such as from about 0.005:1 to about 0.05:1, from about 0.01:1 to about 0.05:1, from about 0.01:1 to about 0.04:1 or from about 0.02:1 to about 0.04:1. In some aspects of the present invention, a second reactor feed stream comprising a mole ratio of acetaldehyde to ethanol in excess of 0.05:1, such as between 0.05:1 and about 0.2:1 can be utilized at one or more injection points in combination with a first reactor feed stream comprising a mole fraction of acetaldehyde to ethanol of less than 0.05:1. In any of the various aspects of the invention, the mole ratio of acetaldehyde to ethanol in any region of the reactor feed section does not differ by more than 50%, 40%, 30%, 20% or 10% from the average mole ratio of acetaldehyde to ethanol in the reactor feed section. In general, the temperature profile in the reactor feed section is such that the temperature in any region of the reactor feed section does not differ by more than 15° C., 10° C. or 5° C. from the average temperature along the length of the reactor feed section.

In any of the various aspects of the present invention, in addition to the above described process variables and combinations thereof, the reaction pressure in the one or more reactors is from about 10 bara to about 200 bara, from about 20 bara to about 200 bara, from about 20 bara to about 150 bara, from about 20 bara to about 100 bara, from about 20 bara to about 80 bara, or from about 25 bara to about 60 bara, such as about 25 bara, 30 bara, 35 bara, 40 bara, 45 bara, 50 bara, 55 bara, 60 bara, 65 bara, 70 bara or 75 bara, and ranges thereof. Further, the reaction temperature in the one or more reactors is from about 50° C. to 450° C., from about 100° C. to about 300° C., from about 150° C. to about 250° C., from about 175° C. to about 350° C., or from about 200° C. to about 300° C., such as about 200° C., 210° C., 220° C., 230° C., 240° C., 250° C., 260° C., 270° C., 280° C., 290° C. or 300° C., and ranges thereof. In aspects of the present invention wherein two or more reactors are used in series, temperature and pressure gradients from the first to last reactor can be used. For instance, the temperature for each reactor in series may be about 5° C., 10° C., 15° C., 20° C., 25° C., 30° C. or 35° C. greater than the temperature in the preceding reactor and the pressure may be about 5 bara, 10 bara, 15 bara or 20 bara greater than the pressure in the preceding reactor. In some aspects of the present invention, as the catalyst deactivates towards the end of a production run, the conversion may be maintained by increasing gradually inlet temperature. For instance, the inlet temperature may be increased by about 10° C., 20° C., 30° C., 40° C., 50° C., 60° C., 70° C., 80° C., 90° C. or about 100° C. from the beginning of a production run to the termination of the production run. In general, the reaction temperature may be controlled such that the reactor system outlet temperature increases by about the same amount. In some aspects of the present invention, the reactor system outlet temperature reaches about 250° C., 260° C., 270° C., 280° C., 290° C., 300° C., 320° C. or 340° C. at the end of the production run.

In any of the various aspects of the present invention, an ethanol conversion of about 10%, 15%, 20%, 25%, 30%, 35%, 40%, 45%, 50%, 55% or 60% is achieved, such as from about 15% to about 40%, from about 20% to about 40%, from about 25% to about 40% or from about 25% to about 35%. A n-butanol yield based on ethanol of about 10%, 15%, 20%, 25%, 30% or 35% is achieved, such as from about 10% to about 35%, from about 10% to about 30%, from about 15% to about 30%, from about 20% to about 30%. Selectivity to n-butanol of about 60%, 65%, 70%, 75%, 80%, 85%, 90% or 95% is achieved, such as from about 65% to about 95%, from about 65% to about 90%, from about 70% to about 90%, from about 75% to about 85%, or from about 80% to about 85%. In some aspects of the present invention, the n-butanol yield based on ethanol is from about 15% to about 25% and the selectivity to n-butanol is from about 70% to about 85%, the n-butanol yield based on ethanol is from about 10% to about 15% and the selectivity to n-butanol is from about 90% to about 95%, or the n-butanol yield based on ethanol is from about 30% to about 35% and the selectivity to n-butanol is from about 65% to about 70%.

The n-butanol reactor product stream typically comprises from about 7 to about 15 mole % or from about 7 to about 10 mole % n-butanol, such as about 7, 8, 9, 10, 11, 12, 13, 14 or 15 mole %; from about 45 to about 75 mole % or from about 50 to about 70 mole % ethanol; from about 0.3 to about 1.5 or from about 0.3 to about 0.9 mole % acetaldehyde, such as about 0.3, 0.4, 0.5, 0.6, 0.7, 0.8, or 0.9 mole %; from about 5 to about 15 mole % water, such as about 5, 10 or 15 mole %; from about 5 to about 25 mole % $H_2$, such as about 5, 7, 9, 11, 13, 15, 17 or 20 mole %; from about 0.1 to about 0.2 ethyl acetate, such as about 0.1, 0.15 or 0.2 mole %; and from about 0.5 to about 6.5 mole % or from about 0.8 to about 6.2 mole % of alcohols other than ethanol and n-butanol, such as about 0.5, 1, 1.5, 3, 5 or 6 mole %.

In some aspects of the present invention as depicted in FIGS. 1 to 6, a splitter fractionation (distillation) column or a preflash fractionation (distillation) column receives and fractionates a reactor product stream comprising n-butanol. In general, the splitter column fractionates the reactor product stream to form a column bottoms stream enriched in relatively high boiling compounds including, but not limited to, n-butanol, i-butanol, hexanol and octanol as compared to the reactor product stream and a splitter column overhead stream enriched in relatively low boiling condensable and gaseous non-condensable compounds including, but not limited to, ethanol, acetaldehyde, ethyl acetate, hydrogen, carbon dioxide, carbon monoxide, methane, ethane and propane as compared to the reactor product stream. In general, the preflash column fractionates the reactor product stream to form a preflash column bottoms stream enriched in high boiling compounds including, but not limited to, n-butanol, i-butanol, hexanol and octanol as compared to the reactor product stream, a preflash column mid-cut stream enriched in compounds including, but not limited to, ethanol, water, acetaldehyde and ethyl acetate as compared to the reactor product stream, and a preflash column overhead stream enriched in gaseous non-condensable compounds including, but not limited to, hydrogen, carbon dioxide, carbon monoxide, methane, ethane and propane as compared to the reactor product stream.

Any column design capable of fractionating the various input streams of the present invention, such as, for instance, the reactor product stream comprising n-butanol, wet ethanol streams, aqueous streams containing organic compounds, n-butanol/hexanol streams, to form the various fractionation streams described herein is suitable for the practice of the present invention, and the selection of suitable fractionating columns is within the purview of those skilled in the art. Generally, fractionation (distillation) columns within the scope of the present invention include, for example, filling plate, valve plate, perforated plate, bubble plate, packed, and wetted-wall (falling film) column. The columns may also comprise conventional components such as, for example, reflux drums, condensers, reboilers or any combination thereof. Columns of the present invention are equipped with one, two or more overhead condensers and one, two or more overhead accumulation tanks and/or separators having gas and liquid (condensate) outlets and reflux capability. In some aspects of the present invention, the distillation column has trays and/or packings internal in each of the stripping section and the enrichment section. The term "internal" used in the present invention means the part in the distillation column where gas and liquid are actually brought into contact with one another. Examples of trays include a bubble-cap tray, a sieve tray, a ripple tray, a ballast tray, a valve tray, a counterflow tray, an Unifrax tray, a Superfrac tray, a Maxfrac tray, a dual flow trays, a grid plate tray, a turbogrid plate tray, a Kittel tray, or the like. Examples of packings include random packings such as a Raschig ring, a Lessing ring, a Pall ring, a Berl saddle, an Intalox saddle, a Dixon packing, a McMahon packing or Heli-Pak, or structured packings such as Mellapak, Gempak, Techno-pack, Flexipac, a Sulzer packing, a Goodroll packing, Glitschgrid or the like. A multi-stage distillation column having both a tray portion and a portion packed with packings can also be used.

In some splitter column aspects of the present invention, the splitter column bottoms, containing the reactor product stream comprising n-butanol, is heated to a temperature of from about 200° C. to about 300° C., or from about 220° C. to about 260° C. by the splitter column reboiler. In some aspects of the present invention, hot oil is used as the reboiler heating medium. The temperature of the top gas fraction passing to the overhead condenser is from about 100° C. to about 180° C., or from about 120° C. to about 160° C. The column pressure is maintained to from about 10 bara to about 30 bara, or from about 15 bara to about 25 bara. In some aspects of the present invention, the overhead condenser cooling temperature is used for splitter column pressure control. The splitter column generates an overhead stream enriched in relatively low boiling condensable compounds and gaseous non-condensable compounds including, but not limited to, ethanol, acetaldehyde, ethyl acetate, hydrogen, carbon dioxide, carbon monoxide, methane, ethane and propane as compared to the reactor product stream. The overhead stream is characterized by an essential absence of high boiling compounds such as n-butanol, n-propanol, i-butanol, hexanol and octanol. In some aspects of the present invention, the overhead stream comprises from about 55 to about 85 mole % or from about 75 to about 80 mole % ethanol; from about 0.2 to about 2 mole % or from about 0.5 to about 1.5 mole % acetaldehyde; from about 0.05 to about 0.5 mole % or from about 0.1 to about 0.2 mole % ethyl acetate; from about 1 to about 15 mole %, from about 2 to about 8 mole % or from about 3 to about 8 mole % hydrogen; from about 0.02 to about 0.1 mole % or from about 0.05 to about 0.1 mole % carbon dioxide; and from about 0.1 to about 1 mole % or from about 0.3 to about 0.8 mole % carbon monoxide. The splitter column generates a bottoms stream enriched in the high boiling compounds as compared to the reactor product stream. In some aspects of the present invention, the bottoms stream comprises from about 80 to about 95 mole % or from about 85 to about 90 mole % n-butanol; from about 0.2 to about 0.5 mole % i-butanol; from about 4 to about 15 mole % or from about 6 to about 8 mole % hexanol; from about 0.2 to about 0.2 mole % octanol.

The splitter column overhead stream, generated from the reactor product stream comprising n-butanol, is passed through a condenser to form a first splitter overhead condensate stream and a second splitter column gas stream. In such aspects of the present invention, the first (condensate) stream typically comprises from about 65 to about 95 mole % or from about 80 to about 90 mole % ethanol; from about 5 to about 20 mole % or from about 10 to about 15 mole % water; from about 0.1 to about 1.5 mole % or from about 0.5 to about 1 mole % acetaldehyde; and from about 0.05 to about 0.5 mole % or from about 0.1 to about 0.3 mole % ethyl acetate. In some aspects of the present invention at least a portion of the first stream may be refluxed to the splitter column and at least a portion is fed forward to an ethyl acetate column for the generation of an ethyl acetate stream and a wet ethanol stream. The selection of a suitable ratio of reflux to feed forward is within the purview of one skilled in the art and varies with, among other factors, the composition of the n-butanol reactor product stream and the desired compositional profile of the first stream. The splitter column overhead gas stream typically comprises, among other components, from about 30 to about 70 mole % or from about 40 to about 60 mole % hydrogen; from about 25 to about 45 mole % or from about 30 to about 40 mole % ethanol; from about 2 to about 10 mole % or from about 3 to about 8 mole % water; from about 0.5 to about 2 mole % or from about 0.8 to about 1.5 mole % acetaldehyde; trace amounts (less than about 0.15 mole %) ethyl acetate; from about 1 to about 8 mole % or from about 2 to about 6 mole % carbon monoxide; and less than about 1, 0.5 or 0.3 mole % of total alcohols other than ethanol.

In some preflash column aspects of the present invention, the column bottoms, comprising the reactor product stream comprising n-butanol, is heated to a temperature of from about 110° C. to about 250° C., from about 130° C. to about 220° C., or from about 160° C. to about 200° C. by the preflash column reboiler. In some aspects of the present invention, hot oil is used as the reboiler heating medium. The temperature of the top gas fraction passing to the overhead condenser is from about 90° C. to about 125° C., from about 95° C. to about 120° C., or from about 100° C. to about 110° C., such as about 105° C. The temperature of the mid-cut stream fed forward to the splitter column is about 130° C. to about 170° C., from about 135° C. to about 165° C., or from about 140° C. to about 160° C., such as about 150° C. The column pressure is maintained to from about 10 bara to about 30 bara, or from about 15 bara to about 25 bara. In some aspects of the present invention, the overhead condenser cooling temperature is used for splitter column pressure control. The preflash column overhead stream is passed through a condenser to form a first overhead stream and a second preflash column overhead gas stream. As compared to the preflash column gas stream, the condensate stream is enriched in ethanol and water. The condensate stream is generally refluxed to the preflash column. In some aspects of the present invention, the condensate stream is totally refluxed to the preflash column. In some aspects of the present invention at least a portion of the first stream may be refluxed to the splitter column and at least a portion is fed forward to a splitter column, ethyl acetate column, extractive distillation or molecular sieves for recovery of non-ethanolic components and/or the recovery of dry ethanol. The selection of a suitable condenser temperature and reflux to feed forward ratio is within the purview of one skilled in the art and varies with, among other factors, the composition of the n-butanol reactor product stream, the desired compositional profile of the condensate and gas streams, and the desired preflash column operating pressure. The preflash column gas stream typically comprises, among other components, from about 30 to about 70 mole % or from about 40 to about 60 mole % hydrogen; from about 25 to about 45 mole % or from about 30 to about 40 mole % ethanol; from about 2 to about 10 mole % or from about 3 to about 8 mole % water; from about 0.5 to about 5 mole % or from about 1 to about 3 mole % acetaldehyde; from about 0.03 to about 0.15 mole % or from about 0.05 to about 0.1 mole % ethyl acetate; from about 1 to about 8 mole % or from about 2 to about 6 mole % carbon monoxide; and less than about 1, 0.5 or 0.3 mole % of total alcohols other than ethanol.

The preflash column mid-cut stream, enriched in compounds including, but not limited to, ethanol, water, acetaldehyde and ethyl acetate as compared to the reactor product stream comprising n-butanol, is fed forward to a splitter column fractionation section. The preflash column bottoms stream, enriched in high boiling compounds including, but not limited to, n-butanol, i-butanol, hexanol and octanol as compared to the reactor product stream, is also fed forward to a splitter column to a fractionation section located between the reboiler and the mid-cut stream inlet. In such aspects of the present invention, the splitter column reboiler heats the bottoms to a temperature of from about 220° C. to about 260° C. or from about 230° C. to about 250° C., such as about 240° C. The temperature of the top gas fraction passing to the overhead condenser is from about 110° C. to about 130° C. or from about 115° C. to about 125° C., such as about 115° C. The temperature of the mid-cut stream is about 150° C. to about 190° C. or from about 160° C. to about 180° C., such as about 170° C. The column pressure is maintained to from about 10 bara to about 30 bara, or from about 15 bara to about 25 bara. The splitter column overhead stream, generated from the preflash column feed, is passed through a condenser to form a first overhead condensate stream and a splitter column overhead gas stream. Compositionally, the overhead, first condensate stream and gas streams are similar to the corresponding streams formed from the n-butanol reactor product stream as described above. The splitter column gas stream may be combined with the preflash column gas stream. The condensate stream may be refluxed to the splitter column, the preflash column, or a combination thereof.

In some aspects of the present invention, the splitter column gas stream or a combination of preflash column and splitter column gas streams may be passed through a second condenser to form a splitter or preflash column second overhead condensate stream and splitter or preflash column second overhead gas stream. Such second overhead condensate streams are characterized as typically comprising, among other components, from about 75 to about 95 mole % or from about 80 to about 90 mole % ethanol; from about 5 to about 20 mole % or from about 10 to about 15 mole % water; from about 1 to about 10 mole %, from about 2 to about 8 mole %, or from about 3 to about 5 mole % acetaldehyde; and from about 0.05 to about 0.5 mole % or from about 0.1 to about 0.3 mole % ethyl acetate. Such second gas streams are characterized as typically comprising, among other components, from about 80 to about 95 mole % or from about 80 to about 90 mole % hydrogen; from about 1 to about 10 mole % or from about 4 to about 8 mole % carbon monoxide; from about 1 to about 15 mole % or from about 2 to about 10 mole % total methane, ethane and propane; less than about 0.2 mole % or less than about 0.1 mole % acetaldehyde; and only trace amounts of ethyl acetate.

In some aspects of the present invention, depicted in FIGS. 1 to 3 and 6, at least a portion of the splitter column overhead condensate stream is fed forward to an ethyl acetate column for the generation of an ethyl acetate stream and a wet ethanol stream. Any column design capable of fractionating a feed stream to form a bottoms stream enriched in water and ethanol as compared to the feed stream and an overhead stream enriched in acetaldehyde and ethyl acetate as compared to the feed stream is suitable for the practice of the present invention. The selection of ethyl acetate fractionating columns is within the purview of those skilled in the art, with suitable columns described above in connection with the splitter column.

In any of the various aspects of the present invention, the ethyl acetate column bottoms (comprising the feed stream) is heated to a temperature of from about 70° C. to about 100° C., or from about 75° C. to about 95° C., by one or more ethyl acetate column reboilers. In some aspects of the present invention, isobutanol column overhead is used as the heating medium in a first reboiler and splitter column overhead is used as the heating medium in a second reboiler. The temperature of the top gas fraction passing to the overhead condenser is from about 30° C. to about 50° C., or from about 35° C. to about 45° C. The column pressure is operated at atmospheric pressure, or under slight positive pressure such from about 1 bara to about 1.5 bara, or from about 1 bara to about 1.2 bara.

The ethyl acetate column generates an overhead stream enriched in acetaldehyde and ethyl acetate as compared to the ethyl acetate column feed stream. In some aspects of the present invention, the overhead stream comprises from about 25 to about 60 mole % or from about 30 to about 50 mole % acetaldehyde; from about 1 to about 40 mole % or from about 15 to about 30 mole % ethyl acetate; and from about 5 to about 35 mole % or from about 20 to about 25 mole % ethanol. The overhead stream is passed through a condenser to form a condensate stream generally correspondingly compositionally to the overhead stream and a gas stream comprising from about 30 to about 60 mole % acetaldehyde; from about 1 to about 10 mole % ethyl acetate; and less than about 5 mole % ethanol. In any of the various aspects of the present invention, at least a portion of the overhead condensate stream and gas stream are purged from the process. In some other aspects of the present invention, the overhead condensate stream may be purified to form an ethyl acetate commodity product.

The ethyl acetate column generates a bottoms stream enriched in ethanol and water as compared to the reactor product stream comprising n-butanol. The bottoms stream typically comprises from about 65 to about 95 mole % or from about 80 to about 90 mole % ethanol; from about 10 to about 25 mole % water; and no more than a trace amount of acetaldehyde and ethyl acetate.

In some aspects of the present invention, depicted in FIGS. 1, 2, 4 and 6, various wet ethanol streams, including the ethyl acetate column bottoms stream, the splitter column overhead stream generated from preflash column mid-cut and bottoms streams, fresh ethanol feed, and a regeneration column overhead stream, may be processed by molecular sieve to generate a dry ethanol feed stream for conversion to butanol. Molecular sieves which are capable of adsorbing the water and optionally other impurities from an admixture thereof with an alcohol are well known. In one aspect, the molecular sieve material is selected to remove water. In some other aspects, the molecular sieve material is selected to remove addition impurities such as acetic acid and/or ethyl acetate from the third distillate to form the anhydrous ethanol composition. The selection criteria may include, for instance, pore size and volume characteristics. Typically, such molecular sieves are crystalline, although the particular sieve employed is not critical. Such sieves should, however, be capable of adsorbing at least about 2 w/w, from about 2 to about 30% w/w, or from about 5 to about 25% w/w under the adsorption conditions. Suitable molecular sieves include a zeolitic molecular sieve having an average pore diameter of about 3 Angstroms. Typical examples of such molecular sieves are the A type zeolites, such as 3 A, 4 A and 5 A. Other suitable molecular sieves include inorganic adsorbents such as lithium chloride, silica gel, activated alumina, and/or bio-based adsorbents such as corn grits. The molecular sieves may be configured in a molecular sieve bed and multiple molecular sieve beds may be employed sequentially or in a counter-current arrangement.

In any of the various molecular sieve aspects of the present invention, one or more wet ethanol feed streams described herein are purified by molecular sieve to generate a dry ethanol stream for conversion to n-butanol and a molecular sieve wet ethanol stream containing removed water that may be processed for ethanol recovery, such as by a regeneration column. Wet ethanol streams include ethyl acetate column bottoms stream, splitter column mid-cut stream, fresh ethanol feed stream, and regeneration column overhead stream. The dry ethanol stream is characterized as comprising from about 88 to about 99.9 mole %, from about 98 to about 99.9 mole % or from about 99 to about 99.8 mole % ethanol; less than about 5 mole %, from about 0.05 to about 5 mole %, from about 0.1 to about 1 mole % or from about 0.1 to about 0.3 mole % water; less than about 0.5 mole % or less than about 0.3 mole % alcohol other than ethanol; and only trace amounts (i.e., less than about 0.05 mole %) of acetaldehyde and ethyl acetate. The molecular sieve wet ethanol stream typically comprises from about 35 to about 50 mole % or about 40 to about 45 mole % ethanol; from about 50 to about 65 mole % or about 55 to about 60 mole % water; and trace amounts (less than about 0.05 mole % each) of other compounds.

The molecular sieve wet ethanol stream may be processed in a regeneration column to fractionate the feed stream into recovered alcohol overhead, isoamyl alcohol mid-cut and waste water bottom streams. Any column design as described above capable of fractionating the molecular sieve wet ethanol stream of the present invention is suitable for the practice of the present invention. The regeneration column bottoms (comprising the wet ethanol feed stream from the molecular sieves) is heated to a temperature of from about 110° C. to about 150° C., or from about 120° C. to about 140° C., by a regeneration column reboiler. In some aspects of the present invention, splitter column overhead is used as the heating medium. The temperature of the top gas fraction passing to the overhead condenser is from about 90° C. to about 110° C., or from about 95° C. to about 105° C. The column pressure is operated under a pressure of from about 1.5 bara to about 4 bara, or from about 2 bara to about 3 bara. In some aspects of the present invention, the column pressure is controlled by the overhead condenser. In some further aspects of the present invention, fresh ethanol is introduced into the regeneration column as reflux.

The regeneration column generates an overhead stream consisting essentially of from about 75 to about 85 mole % ethanol and about 15 to about 25 mole % water with only trace amounts of other components. The overhead stream is recycled to the molecular sieves or is processed by extractive distillation to remove water and generate a dry ethanol stream for conversion to n-butanol. The regeneration column further generates a side-draw purge stream comprising from about 1 to about 20 mole % or from about 5 to about 15 mole % isoamyl alcohol (3-methyl-1-butanol), from about 80 to about 99 mole % water and minor amounts of n-butanol and ethanol. The regeneration column generates a bottoms stream consisting essentially of water that is discharged from the process in waste water treatment.

In any of the various aspects of the present invention, fresh ethanol feed may be processed by molecular sieve, by a combination of the regeneration column and molecular sieve, as described above, or by extractive distillation as described herein, to generate a make-up dry ethanol feed stream for conversion to n-butanol. Various sources of fresh ethanol are within the scope of the present invention including bioethanol generated in fermentation processes, ethanol generated by hydration of ethylene, and ethanol generated in catalytic cracking operations. Ethanol produced from renewable bio-based feedstocks (such as from energy crop or cellulosic sources) may contain a variety of impurities such as isoamyl alcohol (3-methyl-1-butanol), tall oil containing esters and rosin acids (cyclic carboxylic acids) alkali metals, phosphorous, fatty acids, ions (organic and inorganic), and surfactants. Fresh ethanol feed is preferably passed through a purification bed prior to dehydration in order to remove and thereby reduce the concentration of various contaminants including ionic contaminants such as organic salts, inorganic salts, anions and cations. Any purification means capable of removing contaminants from fresh ethanol is within the scope of the present invention. In some aspects of the present invention, ion exchange resin may be used for fresh ethanol purification. The ion exchange resin can be suitably placed in a column or a packed bed. The resins are in a cation exchange or anion exchange form, or a combination of the two. In principle, cation-exchange resins remove cations such as sodium, potassium, nitrogen containing compounds, or metal ions (e.g., nickel, iron and chromium), and anion-exchange resins remove anions such as sulfate, chloride, acetate and phosphines. In some optional aspects of the present invention, prior to or after purification treatment, the fresh ethanol may be treated in a treatment zone with a bleaching earth (e.g., bentonite clay) and/or activated carbon. Fresh ethanol may further optionally be filtered prior to or after purification by methods known to those skilled in the art.

In some optional aspects of the present invention, purified fresh ethanol may be added to the process directly in the reactor feed stream instead of being initially dehydrated molecular sieve, by a combination of the regeneration column and molecular sieve, as described above, or by extractive distillation as described herein.

In any of the various aspects of the present invention, at least about 50%, 60%, 65%, or 70%, from about 50% to about 70%, or from about 60% to about 70% of the ethanol present in the reaction mixture is recovered from the reactor product stream and recycled to the reaction mixture.

In some aspects of the present invention, depicted in FIGS. 3, 5, 7 and 8, various wet ethanol streams, including the ethyl acetate column bottoms stream, the splitter column overhead stream generated from preflash column mid-cut and bottoms streams, fresh ethanol feed, and a regeneration column overhead stream, may be processed by extractive distillation to generate a dry ethanol feed stream for conversion to butanol. As is known in the art, extractive distillation is a method of separating close boiling compounds or azeotropes by carrying out the distillation in a multiplate rectification column in the presence of an added extractive agent (solvent) or solvent mixture, wherein the liquid(s) have a boiling point higher than the compounds being separated. When the compounds to be separated normally form an azeotrope, the extractive distillation agent will cause the compounds to boil separately during extractive distillation and thus make possible a separation in a rectification column that cannot be done at all when no agent is present. The extractive agent should boil higher than any of the close boiling liquids being separated and not form minimum boiling azeotropes with them. For instance, the additional solvent preferably employed for the extractive distillation may have a boiling point at the pressure under which the fractionation takes place which is at least 10° C., at least 20° C. or at least 30° C. higher than the boiling point of the highest-boiling component of the mixture to be separated. In general, the extractive agent is introduced near the top of the column and flows downward until it reaches the reboiler. Its presence on each plate of the rectification column alters the relative volatility of the close boiling compounds in a direction to make the separation on each plate greater and thus require either fewer plates to effect the same separation or make possible a greater degree of separation with the same number of plates. Usually the extractive agent is introduced a few plates from the top of the column to insure that none of the extractive agent is carried over with the lowest boiling component. At the bottom of a continuous column, the less volatile components of the close boiling mixtures and the extractive agent are continuously removed from the column.

Examples of suitable extractive agents include glycerin, propylene glycol, N,N-dimethylformamide, dimethylsulfoxide, 1,3-butanediol, 1,4-butanediol, 1,5-pentanediol, hexylene glycol, diethylene glycol, triethylene glycol and tetraethylene glycol. Examples extractive agent mixtures include two, three or four extractive agents selected from phenol, m-p-cresol, o-sec butylphenol, o-tert butylphenol, catechol, hydroquinone, resorcinol, 1-naphthol, 2-naphthol, acetophenone, ethyl acetoacetate, glycerin, dibutylphthalate, dioctylphthalate, diisooctylphthalate, diisodecylphthalate, ethylene glycol phenyl ether, 1,5-pentanediol, diethylene glycol, triethylene glycol, tetraethylene glycol, hexylene glycol, diethylene glycol diethyl ether, butoxypropanol, dipropylene glycol methyl ether, propylene glycol and dipropylene glycol, dimethylsulfoxide, dimethylformamide, 1,3-butanediol, 1,4-butanediol, 1,6-hexanediol, polyethylene glycol 300, diisobutylphthalate, diisodecylphthalate, N,N-dimethylacetamide and 3-chloro-1,2-propanediol. In some aspects of the present invention, the extractive agent is glycerin or ethylene glycol.

Selection of extractive distillation bottoms (reboiler) temperature, gas temperature and column pressure depends on, among other factors, the extractive agent, column feed rate, and desired degree of purity. In the case of glycerin, the column bottoms (comprising the feed stream and extractive agent) are heated to a temperature of from about 150° C. to about 250° C., or from about 180° C. to about 200° C., by one or more reboilers, and the temperature of the top gas fraction passing to the overhead condenser is from about 90° C. to about 110° C., or from about 95° C. to about 105° C. The column pressure is operated at atmospheric pressure, under a slight positive pressure, or at a pressure of from about 1 bara to about 5 bara, or from about 2 bara to about 4 bara. The overhead stream is passed through a condenser to form a dry ethanol stream with a composition as previously described. At least a portion of the non-condensed gasses, including ethyl acetate and acetaldehyde, may be purged from the process. The dry ethanol condensate stream is a source of ethanol for conversion to n-butanol. At least a portion of the condensed ethanol may be refluxed to the extractive distillation column.

The extractive distillation bottoms stream comprises extractive agent (solvent), water and various extracted impurities. The bottoms stream is purified in a regeneration column to generate a purified solvent bottoms stream that is recycled to the extractive distillation column. The regeneration column overhead stream is passed through a condenser, and the condensate (comprising ethanol, water and organic impurities) is fed forward to a water stripper column. At least a portion of the overhead condensate stream may be refluxed to the extractive distillation column. Extractive solvent losses may be made up with fresh extractive agent. In the case of glycerin extractive agent, the extractive distillation column bottoms (comprising contaminated glycerin) is heated to a temperature of from about 120° C. to about 220° C., or from about 150° C. to about 190° C., by one or more regeneration column reboilers, and the temperature of the top gas fraction passing to the overhead condenser is from about 50° C. to about 100° C., or from about 55° C. to about 80° C. The regeneration pressure is operated at a partial vacuum of from about 0.1 bara to about 0.5 bara.

In some other aspects of the present invention, depicted in FIGS. 7 and 8, one or more extractive distillation columns may be used to fractionate the reactor product stream comprising n-butanol to form an overhead stream comprising low boiling organics including ethanol, acetaldehyde, and ethyl acetate and a bottoms stream a bottoms stream comprising water and higher boiling organics including n-butanol, i-butanol, hexanol and octanol.

In some aspects of the present invention, two extractive distillation columns in series are used wherein the first column is operated at a higher pressure than the second column and wherein the bottoms stream from the first column is further purified in the second column. In such aspects, prior to extractive distillation, the reactor product stream comprising n-butanol is passed through one or more condensers to generate gas and condensate streams. The gas stream typically predominantly comprises non-condensable gasses including from about 80 to about 95 mole % or from about 80 to about 90 mole % hydrogen, and from about 1 to about 10 mole % or from about 4 to about 8 mole % carbon monoxide. The gas stream also comprises other gasses such as from about 1 to about 15 mole % or from about 2 to about 10 mole % total methane, ethane and propane; acetaldehyde; and only trace amounts of ethyl acetate. The condensate stream is fed to the first extractive distillation column for the generation of the overhead and bottoms streams. In the case of glycerin extractive agent, in the first extractive distillation column, the bottoms (n-butanol reactor product stream and glycerin) are heated to a temperature of from about 150° C. to about 250° C., or from about 180° C. to about 220° C., by one or more reboilers, and the temperature of the top gas fraction passing to the overhead condenser is from about 30° C. to about 80° C., or from about 40° C. to about 60° C. The column is operated at a pressure of from about 3 bara to about 7 bara, or from about 4 bara to about 6 bara. The overhead stream is condensed in a condenser or two or more sequential condensers to form a dry ethanol condensate stream characterized as comprising from about 98 to about 99.9 mole % or from about 99 to about 99.8 mole % ethanol; from about 0.05 to about 0.5 mole % or from about 0.1 to about 0.3 mole % water; less than about 0.5 mole % or less than about 0.3 mole % alcohol other than ethanol; and only trace amounts (i.e., less than about 0.05 mole %) of acetaldehyde and ethyl acetate. One or more gas streams comprising ethyl acetate and/or acetaldehyde may be purged from the process in the first extractive distillation overhead system.

In such embodiments of the present invention, the first extractive distillation column bottoms stream comprising extractive agent, n-butanol, i-butanol, hexanol, octanol, water, and some reduced quantity of ethanol is subjected to a second extractive distillation. In some aspects of the present invention, the same extractive agent is used in the first and second extractive distillation columns. In the case of glycerin, in the second extractive distillation column, the bottoms (comprising contaminated extractive agent) are heated to a temperature of from about 120° C. to about 220° C., or from about 150° C. to about 190° C., by one or more reboilers, and the temperature of the top gas fraction passing to the overhead condenser is from about 30° C. to about 80° C., or from about 40° C. to about 60° C. The column is operated at a pressure of from about 1 bara to about 3 bara, or from about 1.5 bara to about 2.5 bara. The overhead stream is passed through a condenser and refluxed to the first extractive distillation column. The bottoms stream, predominantly comprising extractive agent, n-butanol, i-butanol, hexanol, octanol and water is processed in a regeneration column as described above to generate a bottoms stream comprising essentially pure extractive agent that is recycled to the first and second extractive distillation column. A regeneration column overhead stream, predominantly comprising n-butanol, i-butanol, hexanol, octanol and water, is condensed and fed forward to a butanol column. The regeneration column bottoms (comprising contaminated extractive agent) is heated to a temperature of from about 180° C. to about 250° C., or from about 200° C. to about 240° C., by one or more reboilers, and the temperature of the top gas fraction passing to the overhead condenser is from about 25° C. to about 40° C., or from about 30° C. to about 30° C. The column is operated under a partial vacuum at a pressure of from about 0.03 bara to about 0.1 bara, or from about 0.05 bara to about 0.08 bara. In such aspects of the present invention, fresh ethanol may be introduced into the process in the first or the second extractive distillation column.

In some aspects of the invention, n-butanol reactor product stream 45 may optionally be processed in a secondary reactor to convert residual aldehyde (acetaldehyde) to ethanol and thereby increase yield. Such an optional aldehyde reactor is depicted as reactor 170 on FIG. 8. Such an aldehyde reactor may optionally be included in any of the various aspects of the present invention, such as the processes depicted in FIGS. 1 to 7. Suitable aldehyde reactors and operation thereof are as described above in connection with reactor system 40.

In some other aspects of the present invention, one extractive distillation column is used. In such aspects, prior to extractive distillation, the n-butanol reactor product stream may be optionally passed through an aldehyde reactor to convert residual aldehyde (e.g. acetaldehyde) to alcohol (e.g., n-butanol) and form a stream having reduced aldehyde content as compared to the reactor product stream comprising n-butanol. In such aspects, prior to extractive distillation, the n-butanol reactor product stream is passed through a first condenser to form gas and condensate streams wherein the gas stream is passed through the aldehyde reactor. In either aspect, the resulting gas and condensate streams are combined and passed through one condenser, or two or more sequential condensers, to generate a gas comprising recyclable hydrogen and a condensate stream for processing by extractive distillation. The gas stream composition is as described above. The condensate stream is fed to the extractive distillation column for the generation of the overhead and bottoms streams. In the case of glycerin extractive agent, the column is operated at a pressure of from about 10 bara to about 30 bara, or from about 15 bara to about 25 bara and corresponding temperatures The overhead stream is condensed in a condenser or two or more sequential condensers to form a dry ethanol condensate stream. The dry ethanol condensate stream composition is as described above. One or more gas streams comprising ethyl acetate and/or acetaldehyde may be purged from the process in the extractive distillation overhead system.

The extractive distillation column bottoms stream comprising extractive agent, n-butanol, i-butanol, hexanol, octanol, and water, and some reduced quantity of ethanol is processed in a regeneration column as described above to generate a bottoms stream comprising essentially pure extractive agent that is recycled to the first and second extractive distillation column. A regeneration column overhead stream, predominantly comprising butanol, i-butanol, hexanol, octanol and water, is condensed and fed forward to a butanol column. Selection of suitable extractive distillation pressure and temperature ranges is within the purview of those skilled in the art based on the extractive agent. In such aspects of the present invention, fresh ethanol may be introduced into the process in the extractive distillation column.

In any of the various aspects of the present invention, a source of dry ethanol is generated in the process for use in forming the reaction mixture, the dry ethanol comprising recovered ethanol and fresh ethanol and characterized as comprising less than about 0.005 moles of acetaldehyde per mole of alcohol, less than about 0.001 moles each of acetaldehyde and ethyl acetate to alcohol, less than about 0.01 total moles of alcohol other than ethanol to ethanol, and the absence of hydrogen and carbon monoxide.

In aspects of the present invention wherein a splitter column or preflash column second overhead condensate stream and a second gas stream are formed, such as depicted in FIGS. 1 to 6, the second overhead condensate stream is characterized as comprising from about 80 to about 90 mole % ethanol, from about 2 to about 8 mole % acetaldehyde, from about 0.05 to about 0.5 mole % ethyl acetate, and the absence of hydrogen and carbon monoxide, and the second gas stream is characterized as comprising from about 80 to about 95 mole % hydrogen, from about 1 to about 10 mole % carbon monoxide, less than about 0.2 mole % acetaldehyde, and no more than a trace amount of ethyl acetate, water and alcohols other than ethanol.

In aspects of the present invention wherein a splitter column or preflash column second overhead condensate stream and a second gas stream are formed, such as depicted in FIGS. 1 to 6, the acetaldehyde concentration in the reaction mixture may be achieved by combining the dry ethanol stream with the splitter column or preflash column second overhead condensate stream. In such aspects of the present invention, isolation of acetaldehyde and reintroduction into the process enables the acetaldehyde concentration in the reaction mixture to be effectively achieved by mixing ratio control. Moreover, removal of acetaldehyde allows for (i) acetaldehyde recovery and recycle and (ii) a second, hydrogen-containing, gas stream that can be further purified prior to recycle into the process. In some acetaldehyde concentration control aspects of the present invention, as described above, second overhead condensate stream 54 comprising recovered acetaldehyde may be optional partially or totally refluxed to ethyl acetate column 60 (FIG. 1 to 3 or 6) or to splitter column 50 (FIGS. 4 and 5). Acetaldehyde not refluxed may be fed forward to the Guerbet reaction in reactor feed streams 36 and 37. The ratio of reflux to feed forward may controlled to achieve a preselected acetaldehyde concentration in the reactor 40 feed streams 36 and 37.

In aspects of the present invention wherein a splitter column or preflash column second overhead condensate stream and a second gas stream are formed, such as depicted in FIGS. 1 to 6, the essential absence of (i.e., no more than a trace amount of) ethyl acetate, water and non-ethanolic alcohols in the reaction mixture may be achieved by the generation of dry ethanol and splitter column or preflash column second overhead condensate streams containing only trace amounts of those compounds.

In aspects of the present invention wherein a splitter column or preflash column second overhead condensate stream and a second gas stream are formed, such as depicted in FIGS. 1 to 6, the hydrogen and carbon monoxide concentration in the reaction mixture may be achieved by combining (i) the dry ethanol and (ii) the splitter column or preflash column second overhead condensate streams with at (iii) at least a portion of the splitter column or preflash column second overhead gas stream.

In some aspects of the present invention, the second overhead gas stream can be incorporated directly into the reaction mixture. Such process options are depicted in FIGS. 1 and 3 to 8 (splitter column second gas stream 21) and FIG. 2 (splitter column second gas stream 55). In some other aspects of the present invention, the second overhead gas stream 21 can be purified (such as by pressure swing adsorption) to generate a stream consisting essentially of hydrogen that is then incorporated into the reaction mixture. Examples of such process options are depicted in FIGS. 1 and 3 to 8. In some other aspects of the present invention, a mixture of purified and unpurified second gas stream can be incorporated into the reaction mixture. In some other aspects of the present invention not depicted in FIGS. 1 to 8, at least a portion of the hydrogen present in the reaction mixture is provided by a source of generated hydrogen. Such hydrogen generators are known to those skilled in the art. In yet other aspects of the present invention, the Guerbet reaction may be conducted in the presence of only recycled hydrogen (i.e., the reaction mixture consists essentially of recovered hydrogen) without the utilization of make-up hydrogen supplied from a source of generated hydrogen.

In some aspects of the present invention, the second overhead gas stream is purified by pressure swing adsorption ("PSA"). Pressure swing adsorption (PSA) processes are known in the art and are used for purifying hydrogen gas. In PSA processes, hydrogen gas included with impurity gases is fed to an adsorption tower filled with an adsorbent. The hydrogen gas passes through the adsorbent at a high pressure, while impurity gases, for example, $N_2$, $CH_4$, CO and $CO_2$ are adsorbed by the adsorbent at high pressure and are purged from the process.

In any of the various stripping column and flash column aspects of the present invention, about 100%, at least about 60%, at least about 65%, at least about 70%, from about 50% to about 100%, from about 50% to about 80% or from about 60 to about 75%, such as about 65% or about 70%, of the hydrogen present in the second gas stream is recovered and recycled to the reaction mixture. Hydrogen concentration in the reaction mixture is controlled based on the rate of hydrogen recovery and recycle rate. For instance, in some aspects of the present invention, in one example, 0.1 moles of hydrogen are recovered and recycled for each mole of ethanol in the Guerbet reaction mixture.

In either aspect of the present invention for processing the n-butanol reactor product stream by extractive distillation, as depicted in FIGS. 7 and 8, condensed regeneration column overhead is fed to an isobutanol column for the fractionation and removal of water therefrom. The overhead stream comprises a water-butanol azeotrope. The stream is passed through a condenser and fed to a separation tank. The butanol phase is refluxed to the butanol column and the water phase is fed forward to a water stripper column. The butanol column bottoms stream, comprising dry n-butanol, is fed to a hexanol column. Selection of suitable isobutanol column pressure and temperature ranges is within the purview of those skilled in the art. The overhead stream, comprising water and minor amounts of n-butanol, is passed through a condenser. A portion of the condensate is recycled to the stripper column and a portion of the condensate is fed as reflux to the first or second extractive distillation column. Selection of suitable stripper column pressure and temperature ranges is within the purview of those skilled in the art.

In such extractive distillation aspects of the present invention, the bottoms (comprising n-butanol bottoms stream from the butanol column) is heated in the hexanol column to a temperature of from about 180° C. to about 200° C., or from about 170° C. to about 190° C., by one or more reboilers, and the temperature of the top gas fraction passing to the overhead condenser is from about 110° C. to about 150° C., or from about 120° C. to about 140° C. The column is operated at a pressure of from about 1.1 bara to about 3 bara, or from about 1.3 bara to about 2 bara. In an optional aspect of the present invention, the hexanol bottoms are heated to a temperature of from about 150° C. to about 190° C., or from about 160° C. to about 180° C., by one or more reboilers, and the temperature of the top gas fraction passing to the overhead condenser is from about 80° C. to about 105° C., or from about 85° C. to about 100° C. The hexanol column is operated under a partial vacuum of about pressure of from about 0.2 to about 0.6 bara, or from about 0.3 bara to about 0.5 bara.

In some aspects of the present invention, depicted in FIGS. 1 to 5, any of the various crude stripper bottoms n-butanol streams may be processed in a hexanol column and, in some aspects, a hexanol column followed by an isobutanol column, to generate a finished n-butanol stream, a hexanol stream and, in some aspects, an i-butanol stream. Suitable hexanol and isobutanol columns are as described above. In the hexanol column, the bottoms (crude n-butanol stream) is heated to a temperature of from about 130° C. to about 190° C., or from about 160° C. to about 180° C., by one or more reboilers, and the temperature of the top gas fraction passing to the overhead condenser is from about 35° C. to about 105° C., or from about 85° C. to about 100° C. The hexanol column is operated under a partial vacuum of about pressure of from about 0.1 to about 0.6 bara, or from about 0.3 bara to about 0.5 bara. The hexanol column overhead stream comprising n-butanol and i-butanol is passed through a condenser. In some aspects of the present invention, a gas stream comprising oxygen, nitrogen and water gas may be vented from the process. At least a portion of the condensate is refluxed to the hexanol column and the remainder is fed to the butanol column. The hexanol column bottoms stream typically comprises from about 70 to about 85 mole % or about 75 to about 80 mole % hexanol; from about 5 to about 15 mole % or from about 8 to about 14 mole % 2-ethyl-1-butanol; from about 2 to about 12 mole % or from about 3 to about 5 mole % octanol; from about 0.5 to about 2.5 mole % or from about 1 to about 2 mole % n-butanol; and minor amounts of other organic compounds. The hexanol stream can optionally be further processed to separate the various components or be incinerated.

In the isobutanol column, the bottoms (crude hexanol column overhead condensate) is heated to a temperature of from about 100° C. to about 140° C., or from about 110° C. to about 130° C., by one or more reboilers, and the temperature of the top gas fraction passing to the overhead condenser is from about 80° C. to about 110° C., or from about 95° C. to about 105° C. The isobutanol column is operated under a pressure of from about 1 to about 2 bara, or from about 1.1 bara to about 1.5 bara. The isobutanol column overhead stream predominantly comprises ethanol, n-propanol, i-butanol and 2-butanol, and only trace amounts of n-butanol. The overhead stream is passed through a condenser and is recycled to the ethyl acetate column, splitter column or extractive distillation column as reflux. Butanol column bottoms stream consists of finished n-butanol comprising greater than 99 mole %, greater than 99.5 mole %, such as from 99 to 99.9 or from 99.5 to 99.9 mole % n-butanol with trace amounts of i-butanol, 3-methyl-1-butanol and 2-butanol.

In one process option depicted in FIG. 6, but applicable to any of the various aspects of the present invention, any of the various crude stripper bottoms n-butanol streams may be processed in an isobutanol column to generate a bottoms stream predominantly comprising n-butanol and hexanol, and an overhead stream predominantly comprising i-butanol. The isobutanol column bottoms stream is fed forward to a butanol column to generate a bottoms stream predominantly comprising hexanol and an overhead stream comprising substantially pure n-butanol product.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

In the following examples 1 to 12, "Exp" refers to experiment number, "° C." refers to the reaction temperature, "Bar" refers to the reaction pressure, "EtOH rate" refers to the ethanol feed rate in moles per hour, "H$_2$/EtOH" refers to the mole ratio of hydrogen to ethanol, "LHSV" refers to reactor liquid hourly space velocity, "x-EtOH" refers to the ethanol conversion rate, "s-BuOH" refers to selectivity to butanol, "Yield" refers to butanol yield, "AA/EtOH" refers to the mole ratio of acetaldehyde to ethanol, "CO/EtOH" refers to the mole ratio of carbon monoxide to ethanol, "CH$_4$/EtOH" refers to the mole ratio of methane to ethanol, "C$_2$H$_6$/EtOH" refers to the mole ratio of ethane to ethanol, "C$_3$H$_8$/EtOH" refers to the mole ratio of propane to ethanol,

Example 1

In a fixed-bed reactor, made out of 154-cm long and 2.5 cm diameter stainless steel reactor, a constant flux of the reactants contacted with 100 g of a metal oxide Guerbet catalyst comprising palladium. The reactor was connected to a synthesis loop, containing a pressure meter (manometer), a regent input connector and an outlet connector. Reactor operating pressure was controlled by a valve sited at the outlet stream. After the desired operating pressure was achieved, reagent was introduced to the reactor synthesis loop. The composition of the outlet stream was measured by gas chromatography in a GC-Agilent 7890N equipped with a FID and TCD detector, a capillary column Rt-U PLOT of 30 m and two packed columns in series (PORAPPACK QS, 3.6-m long, and CARBOXEN 1000, 4.5-m long).

The ethanol conversion, butanol selectivity and butanol yield results, measured after it was determined that the outlet stream composition was stable, are reported in Table 1A below. The ratios of n-butanol to hexanol (BuOH/HexOH), octanol (BuOH/OctOH), i-Butanol (BuOH/iBuOH), 2-Butanol (BuOH/2-BuOH) and 2-ethyl-1-butanol (BuOH/2-Et-1-BuOH) in the product stream are reported in Table 1B below.

TABLE 1A

| | Feed Stream | | | | | Product Stream | | |
|---|---|---|---|---|---|---|---|---|
| Exp | ° C. | Bar | EtOH rate | H$_2$/EtOH | LHSV | x-EtOH | s-BuOH | Yield |
| 101 | 220 | 28 | 2.84 | 0.4 | 1.4 | 5.76 | 79.30 | 4.57 |
| 102 | 240 | 28 | 2.84 | 0.4 | 1.4 | 12.08 | 78.56 | 9.49 |
| 103 | 250 | 28 | 2.84 | 0.4 | 1.4 | 15.70 | 77.44 | 12.16 |
| 104 | 250 | 28 | 3.49 | 0.39 | 1.75 | 14.48 | 77.48 | 11.22 |
| 105 | 250 | 40 | 3.49 | 0.39 | 1.75 | 12.31 | 77.52 | 9.54 |
| 106 | 250 | 50 | 3.49 | 0.39 | 1.75 | 11.65 | 78.25 | 9.12 |
| 107 | 220 | 30 | 2.84 | 0.1 | 1.4 | 10.20 | 76.70 | 7.82 |
| 108 | 220 | 28 | 2.84 | 0.4 | 1.4 | 5.76 | 79.30 | 4.57 |
| 109 | 250 | 28 | 2.84 | 0.4 | 1.4 | 15.70 | 77.44 | 12.16 |
| 110 | 250 | 28 | 3.49 | 0.39 | 1.75 | 14.48 | 77.52 | 11.23 |
| 111 | 245 | 45 | 3.00 | 0.5 | 1.5 | 10.94 | 81.30 | 8.89 |
| 112 | 230 | 30 | 2.40 | 0.4 | 1.2 | 9.81 | 79.15 | 7.76 |
| 113 | 230 | 60 | 3.58 | 0.2 | 1.8 | 4.92 | 83.70 | 4.12 |
| 114 | 230 | 30 | 3.58 | 0.8 | 1.8 | 4.71 | 82.43 | 3.88 |
| 115 | 230 | 60 | 2.40 | 0.8 | 1.2 | 4.60 | 71.07 | 3.27 |
| 116 | 260 | 30 | 2.40 | 0.8 | 1.2 | 13.28 | 78.78 | 10.46 |
| 117 | 260 | 60 | 3.58 | 0.8 | 1.8 | 10.04 | 83.85 | 8.42 |
| 118 | 245 | 45 | 3.00 | 0.5 | 1.5 | 9.04 | 82.06 | 7.42 |
| 119 | 260 | 60 | 2.40 | 0.2 | 1.2 | 21.24 | 78.59 | 16.69 |
| 120 | 260 | 30 | 3.58 | 0.2 | 1.8 | 18.63 | 76.49 | 14.25 |
| 121 | 260 | 60 | 2.40 | 0.2 | 1.2 | 18.53 | 79.24 | 14.68 |
| 122 | 230 | 30 | 3.58 | 0.26 | 1.8 | 6.71 | 80.81 | 5.42 |

TABLE 1B

| Exp | BuOH/HexOH | BuOH/OctOH | BuOH/iBuOH | BuOH/2-BuOH | BuOH/2-Et-1-BuOH |
|---|---|---|---|---|---|
| 101 | 18.44 | 454.97 | 323.80 | >1000 | 99.85 |
| 102 | 14.64 | 198.17 | 440.04 | 240.45 | 78.81 |
| 103 | 13.72 | 168.08 | 436.84 | 258.30 | 74.41 |
| 104 | 14.23 | 182.98 | 451.05 | 250.52 | 80.92 |
| 105 | 15.51 | 212.50 | 442.88 | 236.81 | 91.01 |
| 106 | 15.82 | 231.86 | 621.89 | 229.92 | 94.34 |
| 107 | 10.83 | 112.23 | 290.73 | >1000 | 55.33 |
| 108 | 18.44 | 454.97 | 323.80 | >1000 | 99.85 |
| 109 | 13.72 | 168.08 | 436.84 | 258.30 | 74.41 |
| 110 | 14.23 | 182.98 | 451.05 | 250.52 | 80.92 |
| 111 | 16.91 | 266.65 | 583.66 | 214.09 | 94.79 |
| 112 | 15.66 | 240.96 | 339.75 | 218.56 | 87.68 |
| 113 | 24.84 | 633.96 | 379.03 | 155.18 | 146.80 |
| 114 | 33.86 | 1104.27 | 378.20 | 107.06 | 201.66 |
| 115 | 30.94 | 1902.63 | 529.77 | 105.50 | 210.25 |
| 116 | 24.88 | 469.54 | 464.80 | 127.84 | 146.85 |
| 117 | 29.37 | 801.26 | 547.82 | 122.70 | 184.25 |
| 118 | 21.46 | 399.23 | 437.18 | 136.70 | 140.03 |
| 119 | 11.30 | 122.25 | 726.00 | 244.37 | 66.52 |
| 120 | 12.17 | 134.55 | 422.38 | 209.57 | 78.21 |
| 121 | 12.17 | 145.28 | 764.18 | 230.90 | 74.47 |
| 122 | 19.60 | 386.46 | 311.29 | 146.17 | 132.17 |

Example 2

Experiments were performed following the protocol detailed in Example 1. The ethanol conversion, butanol selectivity and butanol yield results are reported in Table 2A below. The ratios of n-butanol to hexanol (BuOH/HexOH), octanol (BuOH/OctOH), i-Butanol (BuOH/iBuOH), and 2-Butanol (BuOH/2-BuOH) in the product stream are reported in Table 2B below.

TABLE 2A

| | Feed Stream | | | | | Product Stream | | |
|---|---|---|---|---|---|---|---|---|
| Exp | ° C. | Bar | EtOH rate | H$_2$/EtOH | LHSV | x-EtOH | s-BuOH | Yield |
| 201 | 245 | 45 | 3.00 | 0.5 | 1.5 | 9.77 | 82.93 | 8.10 |
| 202 | 231 | 60 | 2.40 | 0.4 | 1.2 | 6.19 | 85.00 | 5.26 |
| 203 | 248 | 57 | 2.40 | 0.4 | 1.2 | 12.32 | 82.57 | 10.17 |
| 204 | 244 | 63 | 1.80 | 0.35 | 0.9 | 12.10 | 82.58 | 9.99 |
| 205 | 256 | 75 | 2.00 | 0.35 | 1 | 15.92 | 82.01 | 13.06 |
| 206 | 257 | 30 | 2.40 | 0.42 | 1.2 | 18.11 | 77.39 | 14.02 |
| 207 | 257 | 30 | 3.60 | 0.43 | 1.8 | 14.12 | 78.76 | 11.12 |
| 208 | 260 | 30 | 3.60 | 0.4 | 1.8 | 15.67 | 77.84 | 12.19 |
| 209 | 265 | 75 | 2.40 | 0.4 | 1.2 | 19.11 | 80.30 | 15.35 |
| 210 | 263 | 51 | 1.80 | 0.55 | 0.9 | 21.32 | 79.10 | 16.87 |
| 211 | 254 | 49 | 2.40 | 0.4 | 1.2 | 15.17 | 80.68 | 12.24 |
| 212 | 254 | 40 | 2.40 | 0.4 | 1.2 | 15.93 | 79.79 | 12.71 |
| 213 | 245 | 45 | 3.00 | 0.5 | 1.5 | 9.06 | 82.06 | 7.43 |
| 214 | 260 | 60 | 3.60 | 0.4 | 1.8 | 14.36 | 79.84 | 11.47 |
| 215 | 260 | 30 | 3.60 | 0.4 | 1.8 | 15.77 | 77.28 | 12.18 |
| 216 | 260 | 70 | 3.60 | 0.4 | 1.8 | 15.16 | 77.51 | 11.75 |
| 217 | 245 | 45 | 3.00 | 0.5 | 1.5 | 9.39 | 82.16 | 7.71 |
| 218 | 250 | 50 | 2.40 | 0.4 | 1.2 | 13.11 | 80.54 | 10.56 |
| 219 | 250 | 60 | 2.40 | 0.31 | 1.2 | 13.90 | 81.17 | 11.29 |
| 220 | 250 | 60 | 2.40 | 0.68 | 1.2 | 10.40 | 83.78 | 8.71 |

TABLE 2B

| Exp | BuOH/HexOH | BuOH/OctOH | BuOH/iBuOH | BuOH/2-BuOH | BuOH/2-Et-1-BuOH |
|---|---|---|---|---|---|
| 201 | 18.34 | 258.53 | 584.83 | 139.31 | 122.83 |
| 202 | 22.64 | 477.10 | 425.24 | 134.24 | 142.59 |
| 203 | 16.33 | 224.38 | 481.95 | 171.13 | 118.97 |
| 204 | 15.94 | 203.06 | 513.85 | 164.79 | 101.71 |
| 205 | 14.59 | 170.88 | 530.92 | 185.85 | 91.37 |
| 206 | 12.88 | 125.37 | 359.87 | 171.93 | 83.00 |
| 207 | 15.91 | 192.99 | 339.29 | 174.85 | 106.73 |
| 208 | 14.88 | 171.78 | 335.57 | 161.63 | 98.63 |
| 209 | 13.09 | 146.68 | 544.99 | 201.47 | 83.12 |
| 210 | 12.56 | 129.63 | 504.05 | 193.98 | 77.51 |
| 211 | 14.93 | 181.84 | 436.44 | 177.83 | 96.12 |
| 212 | 14.27 | 168.38 | 408.94 | 176.66 | 91.67 |
| 213 | 20.96 | 374.31 | 466.86 | 132.67 | 141.10 |
| 214 | 13.72 | 146.99 | 461.59 | 178.41 | 94.02 |
| 215 | 13.41 | 132.82 | 359.38 | 169.79 | 91.68 |
| 216 | 14.85 | 136.60 | 347.50 | 159.42 | 102.17 |
| 217 | 19.22 | 296.05 | 421.94 | 138.52 | 131.78 |
| 218 | 14.75 | 163.69 | 457.37 | 173.25 | 97.45 |
| 219 | 13.70 | 161.93 | 485.39 | 190.26 | 89.56 |
| 220 | 19.35 | 298.55 | 600.06 | 148.33 | 131.60 |

Example 3

Experiments were performed following the protocol detailed in Example 1. The ethanol conversion, butanol selectivity and butanol yield results are reported in Table 3A below. The ratios of n-butanol to hexanol (BuOH/HexOH), octanol (BuOH/OctOH), i-Butanol (BuOH/iBuOH), and 2-Butanol (BuOH/2-BuOH) in the product stream are reported in Table 3B below.

TABLE 3A

| | | | Feed Stream | | | | Product Stream | | |
|---|---|---|---|---|---|---|---|---|---|
| Exp | °C. | Bar | EtOH rate | $H_2$/EtOH | AA/EtOH | LHSV | x-EtOH | s-BuOH | Yield |
| 301 | 231 | 60 | 2.38 | 0.4 | 0.01 | 1.2 | 5.66 | 84.57 | 4.79 |
| 302 | 254 | 49 | 2.38 | 0.4 | 0.01 | 1.2 | 15.27 | 81.73 | 12.48 |
| 303 | 254 | 40 | 2.38 | 0.4 | 0.01 | 1.2 | 15.80 | 81.82 | 12.93 |
| 304 | 256 | 75 | 1.98 | 0.35 | 0.01 | 1 | 15.40 | 83.32 | 12.83 |
| 305 | 260 | 30 | 3.56 | 0.4 | 0.01 | 1.8 | 15.42 | 82.23 | 12.68 |
| 306 | 263 | 51 | 1.78 | 0.55 | 0.01 | 0.9 | 20.41 | 81.33 | 16.60 |
| 307 | 265 | 75 | 2.38 | 0.4 | 0.01 | 1.2 | 18.24 | 82.52 | 15.05 |
| 308 | 260 | 30 | 3.56 | 0.2 | 0.01 | 1.8 | 18.43 | 77.65 | 14.31 |
| 309 | 260 | 60 | 3.56 | 0.4 | 0.01 | 1.8 | 13.82 | 82.91 | 11.45 |
| 310 | 260 | 30 | 3.56 | 0.4 | 0.01 | 1.8 | 15.45 | 81.18 | 12.54 |
| 311 | 260 | 60 | 3.56 | 0.8 | 0.01 | 1.8 | 10.65 | 85.75 | 9.13 |

TABLE 3B

| Exp | BuOH/HexOH | BuOH/OctOH | BuOH/iBuOH | BuOH/2-BuOH | BuOH/2-Et-1-BuOH |
|---|---|---|---|---|---|
| 301 | 18.37 | 303.05 | 332.98 | 137.53 | 104.25 |
| 302 | 12.83 | 137.25 | 392.29 | 192.74 | 78.00 |
| 303 | 12.55 | 121.92 | 368.71 | 192.19 | 78.91 |
| 304 | 13.41 | 150.51 | 494.32 | 204.24 | 81.61 |
| 305 | 13.66 | 142.65 | 332.52 | 181.08 | 89.29 |
| 306 | 11.97 | 114.87 | 505.93 | 204.04 | 73.36 |
| 307 | 12.72 | 133.20 | 520.59 | 216.79 | 78.82 |
| 308 | 9.83 | 72.46 | 340.54 | 224.50 | 63.74 |
| 309 | 12.90 | 133.35 | 420.50 | 220.32 | 84.83 |
| 310 | 13.02 | 128.45 | 373.88 | 192.07 | 84.48 |
| 311 | 17.79 | 241.92 | 563.87 | 155.26 | 116.68 |

Example 4

Experiments were performed following the protocol detailed in Example 1. Each experiment was run at 46 Bar, 245° C., 2.6 mol/h EtOH, and 1.5 LHSV The ethanol conversion, butanol selectivity and butanol yield results are reported in Table 4A below. The ratios of n-butanol to hexanol (BuOH/HexOH), octanol (BuOH/OctOH), i-Butanol (BuOH/iBuOH), and 2-Butanol (BuOH/2-BuOH) in the product stream are reported in Table 4B below.

TABLE 4A

| | Feed Stream | | | | | Product Stream | | |
|---|---|---|---|---|---|---|---|---|
| Exp | $H_2$/EtOH | CO/EtOH | $CH_4$/EtOH | $C_2H_6$/EtOH | $C_3H_8$/EtOH | x-EtOH | s-BuOH | Yield |
| 401 | 0.5 | — | — | — | — | 5.66 | 84.57 | 4.79 |
| 402 | 0.5 | 0.077 | 0.012 | 0.0011 | 0.0015 | 15.27 | 81.73 | 12.48 |
| 403 | 0.5 | — | — | — | — | 15.80 | 81.82 | 12.93 |

TABLE 4B

| Exp | BuOH/HexOH | BuOH/OctOH | BuOH/iBuOH | BuOH/2-BuOH | BuOH/2-Et-1-BuOH |
|---|---|---|---|---|---|
| 401 | 12.55 | 114.96 | 350.94 | 149.60 | 80.44 |
| 402 | 13.42 | 145.84 | 373.08 | 150.54 | 88.45 |
| 403 | 12.67 | 121.41 | 370.18 | 159.56 | 83.03 |

Example 5

Experiments were performed following the protocol detailed in Example 1. Experiment A101 was run at 245° C. and all other experiments at 260° C., Experiments A211 and A212 contained BuOH in the feed at a rate of 1.16 mol/h (38 mol % of alcohol feed) and 3.92 mol/h (51 mol % of alcohol feed), respectively. The results are reported in Tables 5A and 5B below. In Table 5B, the product stream results are reported in mole % wherein PeOH refers to pentanol, 2-Et-1-BuOH refers to 2-ethyl-1-butanol, HexOH refers to hexanol, OctOH refers to octanol, DecOH refers to decanol, DodecOH refers to dodecanol, and TetOH refers to tetradecanol.

TABLE 5A

| | | | Feed Stream | | | | | | Product Stream | | |
|---|---|---|---|---|---|---|---|---|---|---|---|
| Exp | Bar | EtOH rate | H$_2$/EtOH | LHSV | CO/EtOH | AA/EtOH | H$_2$O/EtOH | xEtOH | sBuOH | Yield |
| A101 | 45 | 3.00 | 0.5 | 1.6 | — | — | — | 11.47 | 80.38 | 9.22 |
| A102 | 30 | 3.00 | 0.5 | 1.6 | — | — | — | 20.67 | 72.82 | 15.06 |
| A103 | 40 | 3.00 | 1 | 1.6 | — | — | — | 15.16 | 78.94 | 11.97 |
| A201 | 31 | 3.00 | 0.5 | 1.6 | — | — | 0.01 | 22.77 | 65.14 | 14.83 |
| A202 | 41 | 3.00 | 1 | 1.6 | — | — | 0.01 | 17.10 | 73.69 | 12.60 |
| A203 | 33 | 3.30 | 0.5 | 1.8 | — | — | 0.05 | 15.12 | 64.50 | 9.75 |
| A204 | 43 | 3.30 | 1 | 1.8 | — | — | 0.05 | 10.46 | 72.06 | 7.54 |
| A205 | 33.1 | 3.03 | 0.57 | 1.7 | — | 0.05 | — | 19.64 | 71.34 | 14.01 |
| A206 | 45 | 3.00 | 1.14 | 1.7 | — | 0.05 | — | 10.62 | 79.46 | 8.44 |
| A207 | 30 | 2.81 | 0.5 | 1.6 | — | 0.05 | — | 19.35 | 71.43 | 13.82 |
| A208 | 40 | 2.85 | 1 | 1.6 | — | 0.05 | — | 15.57 | 74.33 | 11.57 |
| A209 | 30 | 2.68 | 0.5 | 1.6 | — | 0.10 | — | 28.99 | 48.36 | 14.02 |
| A210 | 40 | 2.68 | 1 | 1.6 | — | 0.10 | — | 19.53 | 58.61 | 11.44 |
| A211 | 30 | 1.87 | 0.5 | 2.0 | — | — | — | 45.76 | 33.44 | 15.30 |
| A212 | 40 | 3.75 | 0.5 | 4.0 | — | — | — | 15.42 | 0.00 | 0.00 |
| A213 | 31 | 3.00 | 0.5 | 1.6 | 0.05 | — | — | 7.96 | 76.03 | 6.05 |
| A214 | 41 | 3.00 | 1 | 1.6 | 0.05 | — | — | 6.60 | 76.25 | 5.03 |

TABLE 5B

| Exp | BuOH | PenOH | 2-Et-1-BuOH | HexOH | OctOH | DecOH | DodecOH | TetOH |
|---|---|---|---|---|---|---|---|---|
| A101 | 80.4 | 0.11 | 1.2 | 8.6 | 0.92 | 0.14 | 0.09 | 0.04 |
| A102 | 72.8 | 0.18 | 1.75 | 12.2 | 2.39 | 0.69 | 0.19 | 0.07 |
| A103 | 78.9 | 0.15 | 1.17 | 8.91 | 1.11 | 0.17 | 0.08 | 0.04 |
| A201 | 65.1 | 0.34 | 2.28 | 13.7 | 3.89 | 2.13 | 1.01 | 0.38 |
| A202 | 73.7 | 0.2 | 1.74 | 11.8 | 2.16 | 0.6 | 0.17 | 0.05 |
| A203 | 64.5 | 0.16 | 2.66 | 15 | 3.67 | 1.25 | 0.43 | 0.18 |
| A204 | 72.1 | 0.2 | 2.02 | 11.6 | 1.83 | 0.35 | 0.11 | 0.06 |
| A205 | 71.3 | 0.19 | 2.43 | 14 | 3.27 | 1.22 | 0.47 | 0.18 |
| A206 | 79.5 | 0.15 | 1.3 | 9.28 | 1.18 | 0.21 | 0.08 | 0.04 |
| A207 | 71.4 | 0.19 | 2.1 | 13.5 | 3.02 | 1.05 | 0.35 | 0.12 |
| A208 | 74.3 | 0.21 | 1.98 | 12.2 | 2.5 | 0.97 | 0.34 | 0.15 |
| A209 | 48.4 | 0.23 | 3.32 | 15 | 5.76 | 4.31 | 4.48 | 3.74 |
| A210 | 58.6 | 0.18 | 3.05 | 14.8 | 4.95 | 0.03 | 2.55 | 1.38 |
| A211 | 33.4 | 0.3 | 5.33 | 36.2 | 7.3 | 1.95 | 0.73 | 0.21 |
| A212 | 0 | 0 | 8.64 | 61.1 | 7.56 | 1.44 | 0.39 | 0.09 |
| A213 | 76 | 0.2 | 0.52 | 4.1 | 0.31 | 0 | 0 | 0 |
| A214 | 76.3 | 0 | 0.42 | 3.11 | 0.17 | 0.07 | 0 | 0.05 |

Experiments A211 and A212 were terminated early because heavy compounds were generated that blocked the GC inlet. Acetaldehyde trials at a mole ratio of 0.2:1 to ethanol were stopped because the temperature increased to more than 30° C. above the set point.

The temperature profile of the reactor was analyzed for experiments A209 and A210, each feed stream comprising a mole ratio of acetaldehyde to ethanol of 0.1:1, and for experiment A207 for a feed stream comprising a mole ratio of acetaldehyde to ethanol of 0.05:1. The results are reported in Table 5C below for temperature (° C.) at the length (cm) from the reactor inlet.

TABLE 5C

| Distance from inlet | A207 | A209 | A210 |
|---|---|---|---|
| 17.5 cm | 249° C. | 250° C. | 250° C. |
| 28.5 cm | 261° C. | 261° C. | 261° C. |
| 39.5 cm | 269° C. | 277° C. | 277° C. |
| 50.5 cm | 265° C. | 270° C. | 269° C. |
| 61.5 cm | 262° C. | 263° C. | 263° C. |
| 72.5 cm | 261° C. | 262° C. | 262° C. |
| 83.5 cm | 262° C. | 262° C. | 262° C. |
| 94.5 cm | 261.5° C. | 261.5° C. | 261.5° C. |
| 105.5 cm | 261° C. | 261° C. | 261° C. |
| 116.5 cm | 260° C. | 260° C. | 260° C. |
| 127.5 cm | 262° C. | 262° C. | Not recorded |

Example 6

Experiments were performed following the protocol detailed in Example 1 but wherein the reactor was a 33 cm long and 0.83 cm diameter stainless steel fixed bed reactor, a constant flow of the reagents and 50 mL/minute of N$_2$ were fed to the reactor, a reactor catalyst loading of 3 grams was used, and a GC-Agilent 6890N apparatus was used. The ethanol conversion, butanol selectivity and butanol yield results are reported in Table 6A below. The ratios of n-butanol to hexanol (BuOH/HexOH), octanol (BuOH/OctOH), i-Butanol (BuOH/iBuOH), and 2-Butanol (BuOH/2-BuOH) in the product stream are reported in Table 6B below wherein "n.d." refers to not detected. Analysis indicated the absence of i-Butanol and 2-Butanol.

TABLE 6A

| Exp | °C. | Bar | EtOH rate | H₂/EtOH | LHSV | AA/EtOH | x-EtOH | x-AA | s-BuOH | Yield |
|---|---|---|---|---|---|---|---|---|---|---|
| B101 | 220 | 76 | 0.079 | 0.95 | 1.2 | 0.01 | 8.3 | 74.9 | 87.04 | 7.2 |
| B102 | 240 | 76 | 0.079 | 0.68 | 1.2 | 0.01 | 9.5 | 60.3 | 84.97 | 8.0 |
| B103 | 250 | 76 | 0.079 | 0.68 | 1.2 | 0.02 | 10.9 | 79.8 | 83.81 | 9.1 |
| B104 | 250 | 76 | 0.079 | 0.95 | 1.2 | 0.02 | 9.0 | 87.3 | 84.11 | 7.6 |
| B105 | 250 | 66 | 0.079 | 0.95 | 1.2 | 0.02 | 13.4 | 86.2 | 84.12 | 11.2 |
| B106 | 250 | 76 | 0.056 | 1.01 | 0.93 | 0.11 | 9.4 | 95.2 | 66.21 | 6.2 |
| B107 | 220 | 76 | 0.056 | 1.45 | 0.93 | 0.11 | 11.6 | 96.0 | 66.48 | 7.7 |

TABLE 6B

| Exp | BuOH/HexOH | BuOH/OctOH | BuOH/2-Et-1-BuOH |
|---|---|---|---|
| B101 | 22.54 | n.d. | 110.81 |
| B102 | 16.60 | n.d. | 92.20 |
| B103 | 13.92 | n.d. | 73.10 |
| B104 | 15.79 | n.d. | 75.92 |
| B105 | 16.14 | n.d. | 78.77 |
| B106 | 5.73 | 36.80 | n.d. |
| B107 | 6.12 | 40.53 | n.d. |

Example 7

Experiments were performed following the protocol detailed in Example 6. Each experiment was run at 229° C.; 46 Bar; 1.4 molar ratio of H2 to EtOH; 1.32 LHSV; and EtOH feed rate of 0.095 mol/h. The ethanol conversion, butanol selectivity and butanol yield results are reported in Table 7A below. The ratios of n-butanol to hexanol (BuOH/HexOH), octanol (BuOH/OctOH), i-Butanol (BuOH/iBuOH), and 2-Butanol (BuOH/2-BuOH) in the product stream are reported in Table 7B below.

TABLE 7A

| Exp | AA/EtOH | CO/EtOH | EA/EtOH | C₃H₇OH/EtOH | i-BuOH/EtOH | MeOH/EtOH | x-EtOH | s-BuOH | Yield |
|---|---|---|---|---|---|---|---|---|---|
| B201 | — | — | — | — | — | — | 16.71 | 78.55 | 13 |
| B202 | 0.01 | 0.15 | — | — | — | — | 15.16 | 57.97 | 9 |
| B203 | 0.01 | — | — | — | — | — | 15.46 | 81.65 | 13 |
| B204 | — | — | 0.0013 | — | — | — | 16.66 | 70.25 | 12 |
| B205 | — | — | — | — | — | — | 17.85 | 75.29 | 13 |
| B206 | — | — | — | 0.0012 | — | — | 19.25 | 75.44 | 15 |
| B207 | — | — | — | — | 0.0006 | — | 18.89 | 74.88 | 14 |
| B208 | — | — | — | — | — | 0.0014 | 19.49 | 74.80 | 15 |

TABLE 7B

| Exp | BuOH/HexOH | BuOH/OctOH | BuOH/iBuOH | BuOH/2-BuOH | BuOH/2-Et-1-BuOH |
|---|---|---|---|---|---|
| B201 | 31.58 | 831.00 | n.d. | 82.31 | 166.95 |
| B202 | 44.21 | n.d. | n.d. | 59.44 | 2478.69 |
| B203 | 28.15 | 601.62 | n.d. | 84.01 | 143.12 |
| B204 | 53.64 | 72148.55 | n.d. | 54.62 | 305.48 |
| B205 | 36.20 | 1019.49 | n.d. | 75.49 | 187.97 |
| B206 | 37.28 | 1081.21 | n.d. | 76.09 | 192.86 |
| B207 | 36.77 | 1041.32 | 20.49 | 82.86 | 199.75 |
| B208 | 36.11 | 864.50 | 1240.21 | 76.30 | 188.88 |

Example 8

Experiments were performed following the protocol detailed in Example 6. Experiments B302 and B304 utilized ethanol feed containing 1475 ppm $H_2O$; <1 ppm S; 0.213 ppm $SO_4$; and 481 ppm other impurities. The ethanol conversion, butanol selectivity and butanol yield results are reported in Table 8A below. The ratios of n-butanol to hexanol (BuOH/HexOH), octanol (BuOH/OctOH), and 2-Butanol (BuOH/2-BuOH) for the product stream are reported in Table 8B below. i-Butanol was not detected.

TABLE 8A

| Exp | °C. | Bar | EtOH rate | H₂/EtOH | LHSV | x-EtOH | s-BuOH | Yield |
|---|---|---|---|---|---|---|---|---|
| B301 | 224 | 56 | 0.076 | 0.71 | 1 | 14.0 | 78.31 | 11 |
| B302 | 220 | 58 | 0.057 | 0.71 | 0.86 | 5.3 | 79.62 | 4 |
| B303 | 233 | 45 | 0.095 | 1.41 | 1.32 | 16.7 | 78.55 | 13 |
| B304 | 229 | 50 | 0.072 | 1.42 | 1.1 | 3.9 | 81.33 | 3 |

TABLE 8B

| Exp | BuOH/HexOH | BuOH/OctOH | BuOH/2-BuOH | BuOH/2-Et-1-BuOH |
|---|---|---|---|---|
| B301 | 21.43 | 405.11 | 118.19 | 110.37 |
| B302 | 22.38 | n.d. | n.d. | 110.33 |
| B303 | 31.58 | 831.00 | 82.31 | 166.95 |
| B304 | 33.75 | n.d. | n.d. | 185.52 |

Example 9

Experiments were performed following the protocol detailed in Example 1 at a reaction temperature of 256° C. and a pressure of 41 bara. No fresh hydrogen feed was introduced into the reactor. The reactor product stream was analyzed at start up (0 hours), 11 hours, 23 hours, 34 hours, 46 hours and 57 hours by GC for parts per million of hydrogen ("$H_2$"), carbon monoxide ("CO"), carbon dioxide ("$CO_2$"), methane ("$CH_4$"), ethane ("$C_2H_6$"), propane ("$C_3H_8$"), and butane ("$C_4H_{10}$"). The results are reported in the table 9A below.

TABLE 9A

| Hours | $H_2$ | CO | $CO_2$ | $CH_4$ | $C_2H_6$ | $C_3H_8$ | $C_4H_{10}$ |
|---|---|---|---|---|---|---|---|
| 0 | 27400 | 521 | 605 | 3660 | 802 | 725 | 165 |
| 11 | 27400 | 404 | 237 | 3070 | 1150 | 639 | 738 |
| 23 | 27200 | 503 | 606 | 3920 | 1350 | 807 | 648 |
| 34 | 27300 | 533 | 582 | 4010 | 1480 | 800 | 761 |
| 46 | 27100 | 542 | 621 | 4180 | 1800 | 843 | 937 |
| 57 | 27100 | 513 | 627 | 4160 | 1940 | 863 | 1080 |

The results indicate that ethane and butane concentrations increase as over time with continuous recycle, but the concentration of hydrogen, carbon monoxide, carbon dioxide methane and propane remain generally constant.

Example 10

Experiments were performed following the protocol detailed in Example 1 at a temperature of 260° C., a pressure of 40 bara and at a LHSV of 1.84. Reactor gas stream and reactor product streams comprising n-butanol were continuously produced. The gas stream was recycled to the reactor and the product stream was fractionated to generate recycle ethanol and a product stream comprising n-butanol among other compounds. A mole ratio of hydrogen to ethanol of 0.4:1 was used in the reaction. No fresh hydrogen feed was introduced into the reactor. After operating times of start-up (i.e., fresh catalyst), 755 hours, 778 hours, 789 hours, 801 hours and 813 hours the gas and product stream comprising n-butanol were analyzed. The CO and $CO_2$ concentrations (in mole %) are reported in the table 10A below. The reactor product stream composition is also reported in the table below including the (i) the percent ethanol conversion ("xEtOH %"); (ii) ethyl acetate concentration ("EAc"), acetaldehyde concentration ("AA"), 2-butanol concentration ("2-BuOH"), n-butanol concentration ("n-BuOH"), pentanol concentration ("PentOH"), 2-ethyl-1-butanol concentration ("2-Et-1-BuOH"), hexanol concentration ("HexOH"), 2-ethyl hexanol concentration ("2-Et-HexOH"), octanol concentration ("OctOH"), 2-ethyl-1-octanol concentration ("2-Et-1-OctOH"), decanol concentration ("DecOH"), and dodecanol concentration ("DodecOH") are reported in mole %; and (iii) butanol yield (BuOH %).

TABLE 10A

|  | Fresh | 755 hours | 778 hours | 789 hours | 801 hours | 813 hours |
|---|---|---|---|---|---|---|
| CO | 0 | 0.022 | 0.022 | 0.051 | 0.031 | 0.024 |
| $CO_2$ | 0.014 | 0.116 | 0.1 | 0.099 | 0.108 | 0.107 |
| xEtOH % | 16.9 | 14.6 | 15.3 | 16.1 | 15.4 | 15.2 |
| EAc | 0.486 | 0.556 | 0.554 | 0.56 | 0.562 | 0.579 |
| AA | 2.81 | 2.88 | 2.95 | 2.88 | 3.06 | 3.22 |
| 2-BuOH | 1.08 | 1.02 | 1.18 | 1.06 | 1.08 | 1.1 |
| n-BuOH | 76.89 | 78.92 | 77.94 | 77.55 | 77.83 | 77.67 |
| PentOH | 0.165 | 0.066 | 0.214 | 0.174 | 0.176 | 0.185 |
| 2-Et-1-BuOH | 1.46 | 1.34 | 1.41 | 1.46 | 1.41 | 1.36 |
| HexOH | 11.74 | 10.8 | 11.32 | 11.69 | 11.53 | 11.46 |
| 2-Et—HexOH | 0.397 | 0.297 | 0.326 | 0.357 | 0.337 | 0.336 |
| OctOH | 2.2 | 1.77 | 1.97 | 2.09 | 1.96 | 2.03 |
| DecOH | 0.78 | 0.56 | 0.64 | 0.68 | 0.63 | 0.63 |
| 2-Et-1-OctOH | 0.139 | 0.1 | 0.12 | 0.135 | 0.121 | 0.132 |
| DodecOH | 0.278 | 0.211 | 0.231 | 0.241 | 0.229 | 0.208 |
| BuOH % | 13.02 | 11.5 | 11.94 | 12.47 | 12.02 | 11.8 |

The results of this experiment demonstrate that n-butanol can be prepared in high yield and selectivity in a continuous process utilizing only recycled hydrogen (i.e., in the absence of fresh or make-up hydrogen), recycled ethanol, and without purification of recycle gas.

Example 11

Experiments were performed following the protocol detailed in Example 1 and in Example 6. Experiments 1 to 3 were performed according to the Example 1 protocol and Experiments 4 to 6 were performed according to the Example 6 protocol. The results are reported in Table 11A below.

TABLE 11A

| Exp | Catalyst | ° C. | Bar | $H_2$/EtOH | LHSV | x-EtOH | S_BuOH | Yield |
|---|---|---|---|---|---|---|---|---|
| 1 | 100 g | 270 | 55 | 0.6 | 0.9 | 32.74 | 69.19 | 22.65 |
| 2 | 100 g | 280 | 60 | 1.1 | 0.93 | 36.05 | 69.54 | 25.07 |
| 3 | 100 g | 280 | 55 | 0.6 | 0.93 | 44.98 | 59.63 | 26.82 |
| 4 | 3 g | 290 | 45 | 0.3 | 0.58 | 46.03 | 67.11 | 30.89 |
| 5 | 3 g | 290 | 45 | 0.2 | 0.78 | 35.94 | 71.35 | 25.65 |
| 6 | 3 g | 279 | 42 | 0.5 | 0.78 | 31.46 | 74.66 | 23.49 |

Example 12

An experiment was done to determine n-butanol purity that could be achieved by distillation of a representative reactor product stream. A reactor product stream was batch distillated in a glass lab column. The lab column was formed with a bruun column with 10 plates and another bruun column with 5 plates, a reboiler, condenser and a solenoid mechanism to set the ratio of distillation. The composition of the reactor product stream and purified reactor product stream as measured by GC analysis is reported in Table 12A below.

TABLE 12 A

| Component | Reactor Product Stream | Purified Reactor Product Stream |
|---|---|---|
| Acetaldehyde | 0.71 | 0 |
| Butyraldehyde | 0.17 | 0 |

TABLE 12 A-continued

| Component | Reactor Product Stream | Purified Reactor Product Stream |
|---|---|---|
| Ethylacetate | 0.66 | 0 |
| Methanol | 0.031 | 0 |
| Ethanol | 77.69 | 0.0013 |
| 2-butanol | 0.031 | 0 |
| Propanol | 0.59 | 0 |
| i-butanol | 0.04 | 0.012 |
| Butanol | 16.3 | 99.95 |
| Ethylbutyrate | 0.083 | 0.013 |
| 3-hexanone | 0.076 | 0.0063 |
| Butylacetate | 0.017 | 0.017 |
| 2-ethyl-1-butene | 0.49 | 0 |
| Hexanol | 2.56 | 0 |
| 2-ethyl-1-hexanol | 0.12 | 0 |
| Ethylenglycol | 0 | 0 |
| Octanol | 0.42 | 0 |
| Decanol | 0 | 0 |

What is claimed is:

1. A continuous process for preparing n-butanol, the process comprising:

forming a reaction mixture comprising ethanol, hydrogen, water and acetaldehyde, the reaction mixture comprising a mole ratio of hydrogen to ethanol of from 0.1:1 to about 5:1, a mole ratio of acetaldehyde to ethanol of from about 0.001:1 to about 0.1:1, and a mole ratio of water to ethanol of less than 0.05:1; and contacting the reaction mixture with a Guerbet catalyst in a gas phase reactor having a fixed catalyst bed at a reaction temperature of from about 50° C. to about 450° C. and a reaction pressure of from about 1 MPa absolute (10 bara) to about 20 MPa absolute (200 bara) to form a reactor product stream comprising n-butanol, wherein the n-butanol yield based on ethanol is from about 10% to about 35% and wherein the selectivity to n-butanol is from about 65% to about 95%.

2. The process of claim 1 wherein the mole ratio of hydrogen to ethanol is from about 0.1:1 to about 0.6:1.

3. The process of claim 1 wherein the mole ratio of acetaldehyde to ethanol is from about 0.001:1 to about 0.005:1 or from about 0.005:1 to about 0.1:1.

4. The process of claim 1 wherein the reactor product stream further comprises hydrogen, wherein hydrogen is recovered from the reactor product stream and recycled to the reaction mixture and wherein the hydrogen in the reaction mixture comprises at least 60% recovered hydrogen.

5. The process of claim 1 wherein the reactor product stream further comprises ethanol and wherein ethanol is recovered from the reactor product stream and recycled to the reaction mixture and wherein the ethanol in the reaction mixture comprises at least 60% recovered ethanol.

6. The process of claim 1 wherein the Guerbet catalyst is a metal oxide catalyst.

7. The process of claim 6 wherein the metal oxide comprises Pd.

* * * * *